United States Patent [19]
Kupershmidt

[11] Patent Number: 5,448,992
[45] Date of Patent: Sep. 12, 1995

[54] METHOD AND APPARATUS FOR NON-INVASIVE PHASE SENSITIVE MEASUREMENT OF BLOOD GLUCOSE CONCENTRATION

[75] Inventor: Vladimir Kupershmidt, Pleasonton, Calif.

[73] Assignee: Sunshine Medical Instruments, Inc., Sausalito, Calif.

[21] Appl. No.: 71,321

[22] Filed: Jun. 1, 1993

Related U.S. Application Data

[63] Continuation-in-part of Ser. No. 988,715, Dec. 10, 1992, abandoned.

[51] Int. Cl.⁶ ............................................. A61B 5/00
[52] U.S. Cl. .................... 128/633; 128/635; 356/364; 356/368; 356/39
[58] Field of Search ............ 128/633, 664–666; 369/364, 366, 368; 356/39, 40, 41

[56] References Cited

U.S. PATENT DOCUMENTS

| | | | |
|---|---|---|---|
| 4,008,717 | 2/1977 | Kowarski | 128/214 R |
| 4,055,175 | 10/1977 | Clemens et al. | 128/213 |
| 4,240,438 | 12/1980 | Updike et al. | 128/635 |
| 4,401,122 | 8/1983 | Clark, Jr. | |
| 4,458,686 | 7/1984 | Clark, Jr. | 128/635 |
| 4,551,427 | 11/1985 | Draeger et al. | 435/14 |
| 4,627,445 | 12/1986 | Garcia et al. | 128/770 |
| 4,633,087 | 12/1986 | Rosenthal et al. | 250/341 |
| 4,633,878 | 1/1987 | Bombardieri | 128/635 |
| 4,685,463 | 8/1987 | Williams | 128/632 |
| 4,704,029 | 11/1987 | Van Heuvelen | 356/39 |
| 4,796,995 | 1/1989 | Salzman et al. | 356/368 |
| 4,834,532 | 5/1989 | Yount | 356/41 |
| 4,969,115 | 11/1990 | Rosenthal | 364/571.03 |
| 4,975,581 | 12/1990 | Robinson et al. | 250/339 |
| 4,990,772 | 2/1991 | Rosenthal | 250/252.1 |
| 5,028,787 | 7/1991 | Rosenthal et al. | 250/341 |
| 5,059,394 | 10/1991 | Phillips et al. | 422/68.1 |
| 5,072,732 | 12/1991 | Rapoport et al. | 128/653.2 |
| 5,077,476 | 12/1991 | Rosenthal | 250/341 |
| 5,086,229 | 2/1992 | Rosenthal et al. | 250/341 |
| 5,127,405 | 7/1992 | Alcala et al. | 128/633 |
| 5,127,406 | 7/1992 | Yamaguchi | 128/633 |
| 5,137,023 | 8/1992 | Mendelson et al. | 128/633 |
| 5,181,138 | 1/1993 | Davis et al. | 359/239 |
| 5,209,231 | 5/1993 | Cote et al. | 128/633 |
| 5,243,983 | 9/1993 | Terr et al. | 128/633 |
| 5,289,258 | 2/1994 | Szafraniec et al. | 356/350 |

OTHER PUBLICATIONS

Cote et al. "Optical Polarimetric Sensor for Blood Glucose Measurement IEEE 1990", pp. 101–102.

(List continued on next page.)

Primary Examiner—Lee S. Cohen
Assistant Examiner—Robert L. Nasser, Jr.
Attorney, Agent, or Firm—Davis Hoxie; Faithfull & Hapgood

[57] ABSTRACT

A method and apparatus for non-invasive measurement of blood glucose concentration based on producing a polarized-modulated laser beam via a polarizing frequency shifter (24), measuring a phase difference introduced, e.g., by a finger (F) or a ear lobule (E) of a subject, measuring phase difference between a reference signal (SR) and a probe signal (SP), and processing the obtained data which are then presented as blood glucose concentration. The apparatus for the above-mentioned measurements comprises an infrared laser source (22), a polarized frequency shifter (24) which produces a polarized-modulated infrared laser beam, a piezoelectric transducer (26) for driving the polarizing frequency shifter (24), and an optical transducer (30) with a glucose measuring head (32). The latter has an optical input for receiving the laser beam and a balanced receiver (62). During measurement, the finger (F) is inserted into the glucose sensing unit (32), and after passing through the finger, the probe optical beam is converted into an electrical signal, compared with the reference electrical signal, and the obtained phase difference is processed by an electronic signal processing unit (34) which presents the results in the form of blood glucose concentration. Embodiments of the apparatus and method based on measurement of circular dichroism caused by the presence of glucose in blood are included.

68 Claims, 11 Drawing Sheets

OTHER PUBLICATIONS

March et al., "Optical Monitor of Glucose", vol. XXV Trans. Am. Soc. Artif. Intern. Organ., 1979, pp. 28–31.

Kozaitis et al. "Laser Polarimetry For Measurement Of Drugs In The Aqueous Humor", Annual International Conference of the IEEE Engineering in Medicine and Biology Society, vol. 13, No. 4, 1991, pp. 1570–1571.

Arnold et al., "Determination of Physiological Levels of Glucose in an Aqueous Matrix with Digitally Filtered Fourier Transform Near Infrared Spectra", *Anal. Chem.*, vol. 62, No. 14, Jul. 15, 1990, pp. 1457–1464.

Cote et al. "Laser Polarimetry For Glucose Monitoring", Annual International Conference of the IEEE Engineering in Medicine and Biology Society, vol. 12, No. 2, 1990, pp. 476–477.

Hobbs, "Fluorescence Reveals Toxins on Antibody-Coated Fiberoptic Probe" Laser Focus World, May 1992 pp. 83–86.

Lakowicz, "Fluorescence Lifetime Sensing Generates Cellular Images" Laser Focus World, May 1992, pp. 60–62, 65, 66, 68, 70, 72, 75, 77–79, 80.

Cote et al., "Noninvasive Optical Polarimetric Glucose Sensing Using a True Phase Measurement Technique" IEEE Transaction On Biomedical Engineering, vol. 39, No. 7, Jul. 1992, pp. 752–756.

METHOD AND APPARATUS FOR NON-INVASIVE PHASE SENSITIVE MEASUREMENT OF BLOOD GLUCOSE CONCENTRATION

This is a continuation-in-part of application(s) Ser. No. 07/988,715 filed on Dec. 10, 1992, now abandoned.

FIELD OF THE INVENTION

The present invention relates to measuring the concentration of glucose, more particularly to the non-invasive, phase-sensitive measurement of the glucose concentration in blood.

BACKGROUND OF THE INVENTION

As of 1992, more than ten million people in the United States of America suffer from diabetes (an increased level of glucose in the blood) and hypoglycemia (a reduced level of glucose in the blood). Individuals afflicted with either disease in a severe form typically perform an invasive blood glucose level analysis four or more times a day.

Invasive techniques require withdrawal of a blood sample from the patient each time an analysis is to be performed. An accurate laboratory blood analysis requires withdrawing from 5 to 10 ml of blood and analyzing it using a laboratory instrument designed for performing such a biochemical analysis. However, the results of the test often are not available for several hours, and sometimes days. In addition, the instruments necessary to perform such an analysis are expensive and require that the blood samples be taken and analyzed by trained technicians.

Another invasive technique, referred to as a "finger poke" or a "finger stick" uses an integrated, self-contained instrument that evaluates a much smaller blood sample (approximately 0.25 ml). The small blood sample is obtained by puncturing a finger with a small lancet. The sample is then placed on a chemically treated carrier and inserted into the instrument. The finger poke devices normally provide the glucose concentration results in a few moments. However, they are still quite costly for private use, i.e., in the range of several thousand dollars.

More recently, portable finger poke instruments have become available which require the use of single use, disposable, chemically treated carrier "strips." Although the portable instruments have a relatively low cost (about $100 to $300), the cumulative cost to diabetics for the normal supply of disposable carrier "strips" is considerable.

Invasive techniques for glucose analysis are problematic and suffer from poor patient compliance. Many people who would benefit from knowing their glucose concentration are reluctant to have blood withdrawn by a finger poke or a hypodermic needle or have a generalized fear of invasive medical procedures. Still others suffer anxiety in connection with the sampling and worry about the discomfort (pain) and possibility of infection. Another problem is that frequent invasive glucose testing uses up convenient sample sites and complicates further testing until the used convenient sites heal.

Non-invasive methods for measuring blood constituents, including glucose have been described. However, to date none of these techniques has resulted in a commercially useful instrument. The non-invasive monitoring methods are roughly divided into measurements based on either the intensity of light being transmitted through or reflected from the tissue, or the phase shift of modulated light transmitted through the tissue (the "phase-sensitive" measurement).

When light is transmitted through perfused tissue in vivo, e.g., through a patient's finger, it is differently absorbed by the various components illuminated, namely blood, with its many constituent parts, tissue (including protein, fat, water, cholesterol, etc.), cartilage, and bone. The different components thus form an absorption spectrum for each wavelength. The total absorption of a given wavelength of light by all of the components is called "real absorption" and the absorption spectrum may vary for different wavelengths.

The known intensity sensing methods for measuring the level of a blood constituent, including glucose, are based on measuring a real absorption spectrum for blood perfused tissue at two or more different wavelengths, and subtracting therefrom the statistical absorption spectra for each of the various blood components, except for the one component being measured. It is assumed that after such subtraction, the remainder is a real spectrum of the constituent to be measured.

Rosenthal et al. U.S. Pat. No. 5,086,229 refers to such a non-invasive, near-infrared quantitative analysis instrument for measuring blood glucose. The instrument contains a plurality of near-infrared laser sources having different wavelengths of emission and one or a plurality of photodetectors. A blood-containing part, e.g., a finger, is placed between the laser sources and photodetectors. The light sources are illuminated and the wavelengths then transmitted through the blood-containing part are detected. The real absorption spectrums obtained from the photodetector signals are compared with individual statistical absorption spectra of each constituent, which are stored in the memory of the instrument. A glucose level is derived from the comparison.

The intensity measuring instruments, including the Rosenthal instrument, suffer from the following disadvantages. First, because they measure intensity, the noise level of the measured signal is affected by components of the tissue other than blood, and variations in conditions such as background light, tissue temperature, ambient temperature, and the amplitude of the laser source. This results in a poor signal-to-noise ratio. Even the use of the latest up-to-date low-noise electronics would not substantially improve this ratio.

Second, because the subtraction technique is based on statistically derived absorption data for each individual constituent, the results obtained are of necessity statistical. However, the differences between the actual glucose level in blood and the results of statistical measurements may be substantial and significant. In this regard, the absorption due to the glucose concentration is very small compared to other components such that statistical errors may be a greater component of the determined value that the actual glucose component.

The non-invasive phase sensitive measurement methods possess significantly higher sensitivity and a much higher signal-to-noise ratio than intensity-measurement methods. The higher sensitivity is the consequence of the noise sources affecting the amplitude, but not the phase, of a signal.

In phase sensitive techniques, an instrument compares a known reference signal, e.g., a sine wave, with a measurement signal that has been passed through the tissue. The measurement signal will have a time delay (phase shift) relative to the reference signal because of various factors, e.g., a fluorescence time delay, etc. Concentrations of blood constituents then may be obtained from a measurement of the time delay (phase shift).

Cote et al., "Noninvasive Optical Polarimetric Glucose Sensing Using A True Phase Measurement Technique," *IEEE Transactions of Biomedical Engineering*, Vol. 39, No. 7, July 1992, pp. 752–756 ("Cote") refers to passing linearly-polarized light through the anterior chamber of an excised human eye and determining the glucose level of the aqueous eye humor based on the phase shift between the reference signal and the measurement signal that was converted by the glucose. A helium-neon laser beam, coupled through a rotating linear polarizer along with two stationary linear polarizers and two detectors, is used to produce reference and signal outputs. The polarizer was rotated by means of a synchronous electric motor. The amplitudes of these outputs varied sinusoidally with a frequency twice that of the angular velocity of the rotating polarizer. The phase difference of the outputs would be proportional to the rotation of the linear polarization vector passing through the anterior chamber of the eye.

One problem with the Cote apparatus is that it uses a synchronous motor which generates mechanical vibrations which cannot exceed, e.g., 200 Hz. Therefore, the frequency of rotation of the motor falls into the frequency range (1 Hz to 600 Hz) of mechanical vibrations produced by different sources, interferes with those mechanical vibrations, and produces high measurement noise. Consequently, the Cote technique can be implemented only under laboratory conditions where mechanical vibrations can be isolated, and is unsuitable for application in the form of a portable instrument for personal use.

Another problem with the Cote measurement system is that it is based on passing the light through the human eye. It is thus inconvenient for practical self-administration of the test. More important, however, is that the eye is subject to involuntary high-frequency movements (such as microsaccadic movements) which fall into the same frequency range as the rotating frequency of the driving motor of the system and have amplitudes of 1 to 3 min of arc. Should the apparatus be used in vivo, such involuntary eye movements would lead to interference with the measurement signals and would markedly increase the measurement noise.

Still another problem with the Cote system is that the axis of the synchronous motor can be fixed with respect to the direction of propagation of optical signals with an accuracy not exceeding several minutes of arc. This means that using the device requires that a calibration be carried out in real time.

Thus, there is a continuing need for improved non-invasive analytical instruments and methods that would provide essentially the same accuracy as conventional invasive blood glucose tests. There also is a need for non-invasive, low-cost methods and instruments for the measurement of glucose levels in diabetic or hypoglycemic patients. There also is a need for a durable, cost-effective, and environmentally conscious nondisposable apparatus for measuring blood glucose.

Summary of the Invention

It is, therefore, an object of the invention to overcome the disadvantages of existing non-invasive instruments and to provide improved methods and apparatus for the non-invasive phase-sensitive measurement of blood constituents such as glucose.

It is another object of the invention to provide a non-invasive apparatus for measuring blood constituents including glucose based on phase-sensitive measurements that is free of moving mechanical parts, results in low noise measurements, and operates in the frequency range beyond that of mechanical vibrations.

It is another object to provide a portable, non-invasive blood glucose monitor that is suitable for personal use, at home or away.

It is another object to provide a portable blood-monitoring device which obtains glucose level measurements through high-scattering (signal-depolarizing) tissue, and is not restricted for use with the eye. It is another object to provide a non-invasive instrument that obtains glucose level measurements using blood-carrying body parts such as fingers, toes, and earlobes.

Broadly, the invention concerns apparatus and methods for the non-invasive measurement of the concentration of a constituent in blood based on precision, phase sensitive and high signal to noise measurements.

One aspect of the invention is directed to a method for the non-invasive precision phase sensitive measurement of the glucose level in the blood. One such method includes the steps of:

passing a beam emitted by an infrared laser beam source through a polarizing frequency shifter that is driven by a piezoelectric transducer and produces a polarized-modulated beam having a direction of polarization rotating in the plane of polarization with a frequency of rotation falling into a frequency range beyond that of mechanical vibrations;

passing the polarized-modulated beam through an optical transducer which splits the polarized-modulated beam into a reference optical beam and a probe optical beam;

passing the probe optical beam through a blood-carrying body part to form a passed probe optical beam, the above-mentioned optical transducer having a first sensor for measuring the reference optical beam and converting it into a reference electric signal having a phase corresponding to the polarized-modulated optical beam, and a second sensor for measuring the passed probe beam and converting it into a probe electric signal having a phase corresponding to the passed probe beam, the second sensor preferably being made in the form of a balanced receiver, the balanced receiver having means for dividing the passed probe optical beam into a polarized component and a depolarized component, and means for determining a scattering-free probe electric signal having a phase from the balanced receiver; determining a phase difference between the reference electric signal and the probe electric signal; and converting the phase difference into information relating to the concentration of glucose.

The phase difference is preferably measured by subtracting the phase of reference electric signal from the phase of the scattering-free probe electric signal. The blood-carrying body part may be any well perfused tissue in which blood vessels are distributed with high density such as an appendage, e.g., finger, earlobe, toe or bridge of the nose. In the case of a measurement carried out with a finger, the laser beam is preferably transmitted through the nail-bed, which is especially concentrated with blood vessels.

BRIEF DESCRIPTION OF DRAWINGS

The above and other objects and advantages of the invention will be apparent upon consideration of the following detailed description taken in conjunction with the accompanying drawing, in which like reference characters refer like parts throughout, and in which.

DETAILED DESCRIPTION OF THE INVENTION

Figure 1:
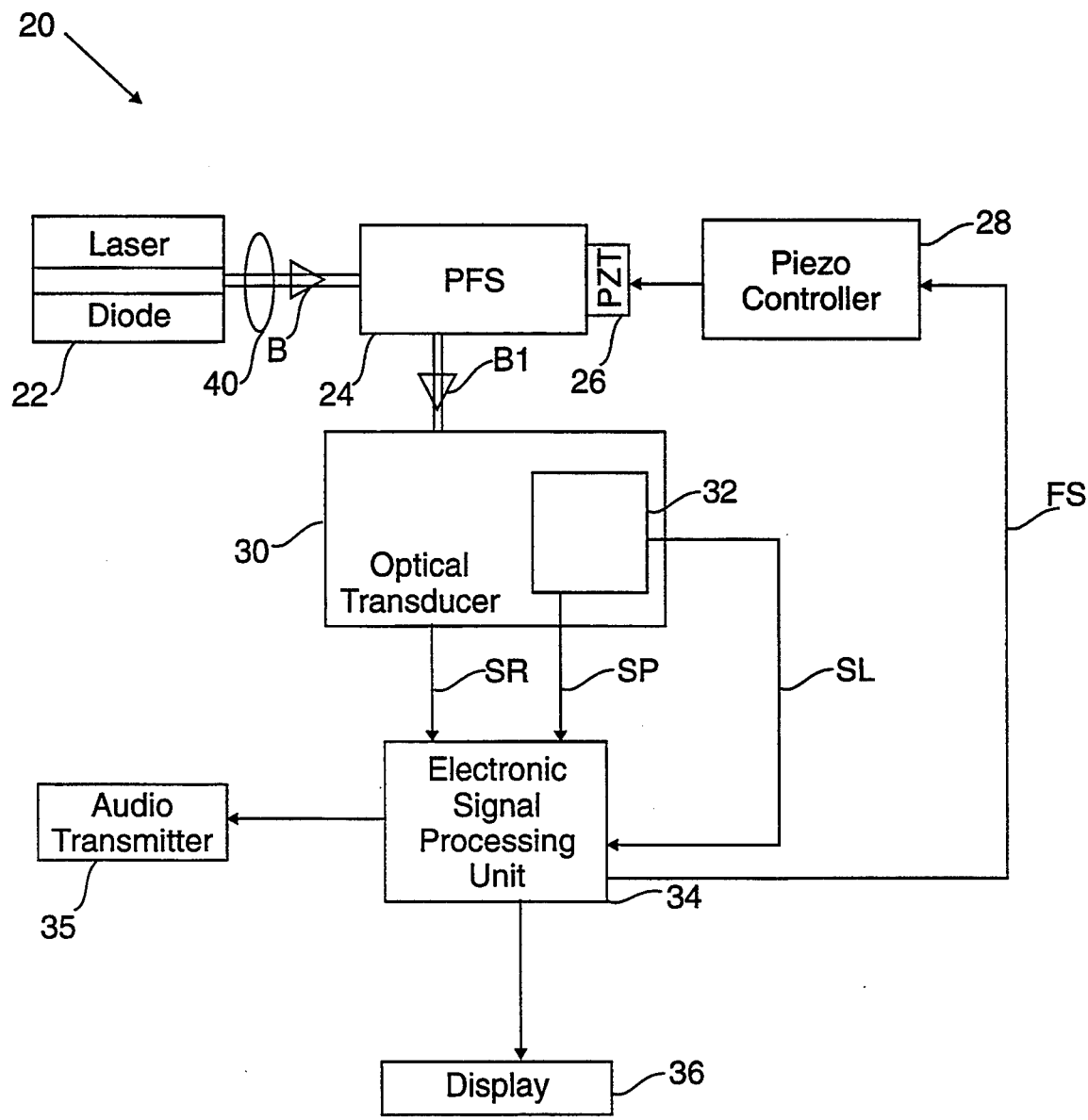
FIG. 1 is a block diagram of an apparatus in accordance with a preferred embodiment of the present invention.

Embodiment of Non-Invasive Apparatus with Polarizing Frequency Shifter for Measuring Polarization Rotation Angle
Embodiment of Non-Invasive Apparatus with Polarizing Frequency Shifter for Measuring Circular Dichroism A preferred embodiment of a non-invasive apparatus in accordance with the present invention is shown in FIG. 1. The apparatus, which is designated in general by reference numeral 20, including a light source 22, a polarized frequency shifter ("PFS") 24, an optical transducer unit 30, an electronic signal processing unit 34, and optionally, one or both of an audio transmitter 35 and a visual display device 36.

Visual display device 36 may be a conventional liquid crystal display or a paper printer. Audio transmitter 35 may be a speaker (or microphone transducer) that indicates audibly the measured value (and, optionally, some indication of the range of normal values) for visually-impaired individuals. In the drawings, optical signals are shown by double lines and electrical signals are shown by single lines.

Light source 22 is preferably a laser source which produces a laser beam, more preferably a laser diode. Laser source 22 has a power-supply unit (not shown) and a collimating lens 40 which produces a collimated optical beam B (1 to 3 mm) with low divergence. The wavelength range is selected to correspond to a known wavelength range that includes a peak of the optical rotation characteristic of the component to be measured. For measuring blood glucose, laser source 22 operates in the wavelength of 750 to 1000 nm, e.g., 850 nm (the near-infrared range) and preferably with a low-noise intensity and phase variation. One such laser diode is available from Spectra Diode Labs, San Jose, Calif. It should be understood that other light sources and other wavelength ranges corresponding to other optical activity peaks for glucose (and similar peaks for other blood constituents) could be used.

PFS 24 receives collimated optical beam B and has a piezoelectric transducer ("PZT") 26, which is controlled by a piezoelectric controller 28. Piezoelectric controller 28 is a conventional circuit that generates a modulating signal, e.g., a sawtooth or triangular waveform at a selected frequency f, preferably responsive to a feedback control signal FS from electronic signal processing unit 34 (as described below), and causes PZT 26 to vibrate accordingly. PZT 26 is used to impart a phase modulation to a component of optical beam B and PFS 24 produces a linearly polarized-modulated optical beam B1 having a direction of polarization which rotates in the plane of polarization, which is perpendicular to the direction of its propagation with a frequency equal to one-half that of PZT 26. Optical beam B1 is sent to optical transducer 30.

Optical transducer 30 receives optical beam B1 and produces a reference electric signal SR corresponding to the phase of optical beam B1, a polarized electric signal SP corresponding to the phase of optical beam B1 after it has passed through blood-carrying tissue, which includes a phase shift introduced by glucose (described in detail below), and an electric signal SL, having an amplitude proportional to the thickness of the measured blood-carrying tissue, e.g., a finger. Optical transducer 30 also includes a glucose measuring head 32 which receives the blood-carrying tissue to be measured. Head 32 may be either securely attached to optical transducer 30 (shown in FIG. 1) or physically disconnected from optical transducer 30 for remote use and coupled to transducer 30 by an optical fiber (shown in FIG. 6A).

Electronic signal processing unit 34 is connected to optical transducer 30, receives electric signals SR, SP, and SL and provides feedback signal FS. Unit 34 processes signals SR and SP and produces a measurement phase difference signal $S\Theta$. The measurement signal phase difference $\Theta_M$ is then taken together with signal SL and calibration data (which provides information regarding the effective thickness of the blood-carrying body) and converted into information about the glucose concentration. The information may be displayed, e.g., in a decimal digital form on visual display 36, which is connected to electronic signal processing unit 34. Feedback signal FS is used to provide a linear motion of piezoelectric transducer 24 with a fixed frequency f and to avoid hysteresis.

Figure 6:
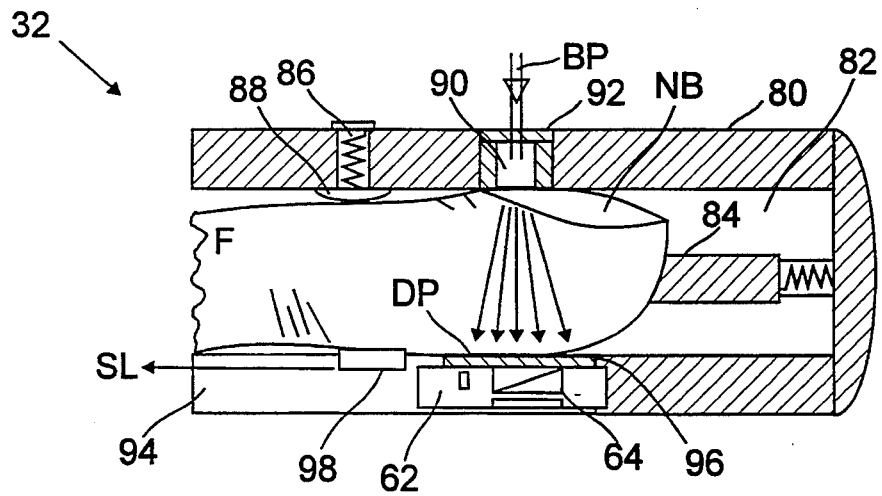
FIG. 6 is a schematic structural view of an embodiment of a built-in glucose measuring head of FIG. 1.
Figure 6A:
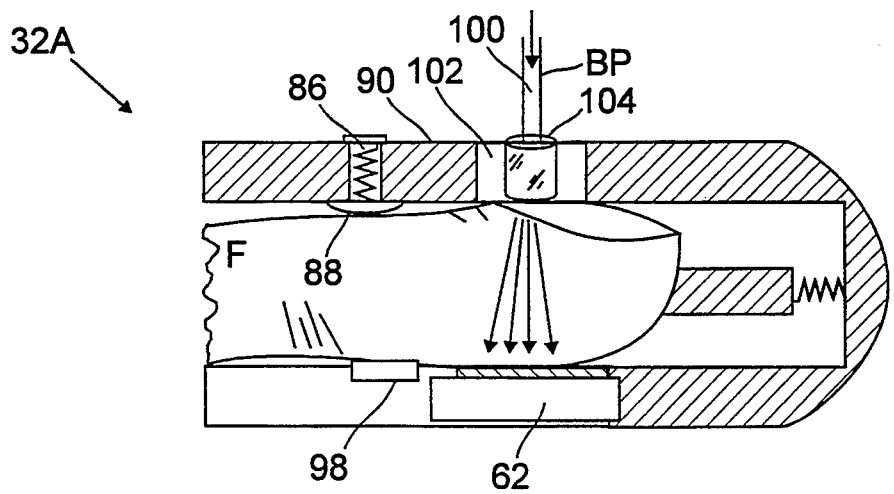
FIG. 6A is a schematic structural view of another embodiment of a remotely-located glucose measuring unit of FIG. 1.
Figure 6B:
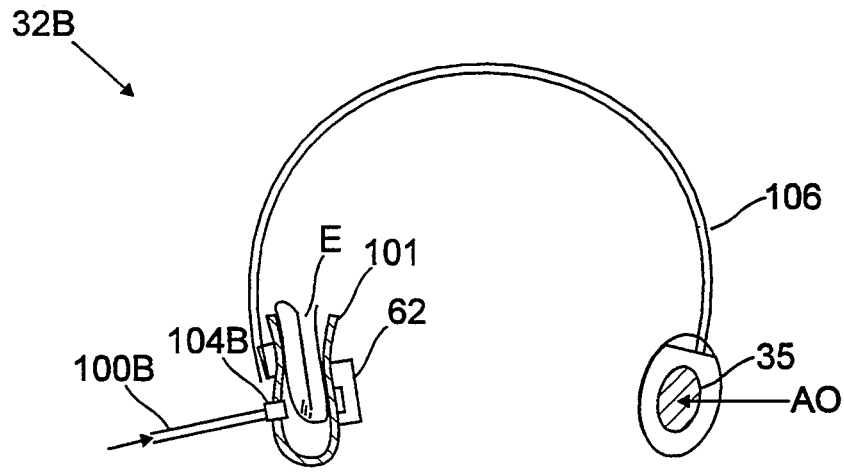
FIG. 6B is a schematic structural view of another embodiment of a glucose measuring head of FIG. 1.

Because in many cases people suffering from diabetes have poor vision, signal processing unit 34 also (or alternatively) may be connected to audio transmitter 35 having an audio output AO (see FIG. 6B). Audio transmitter 35 may repeat the glucose information in an audible form, e.g., by synthesized speech as is conventionally used in the telecommunications field.

Figure 2:
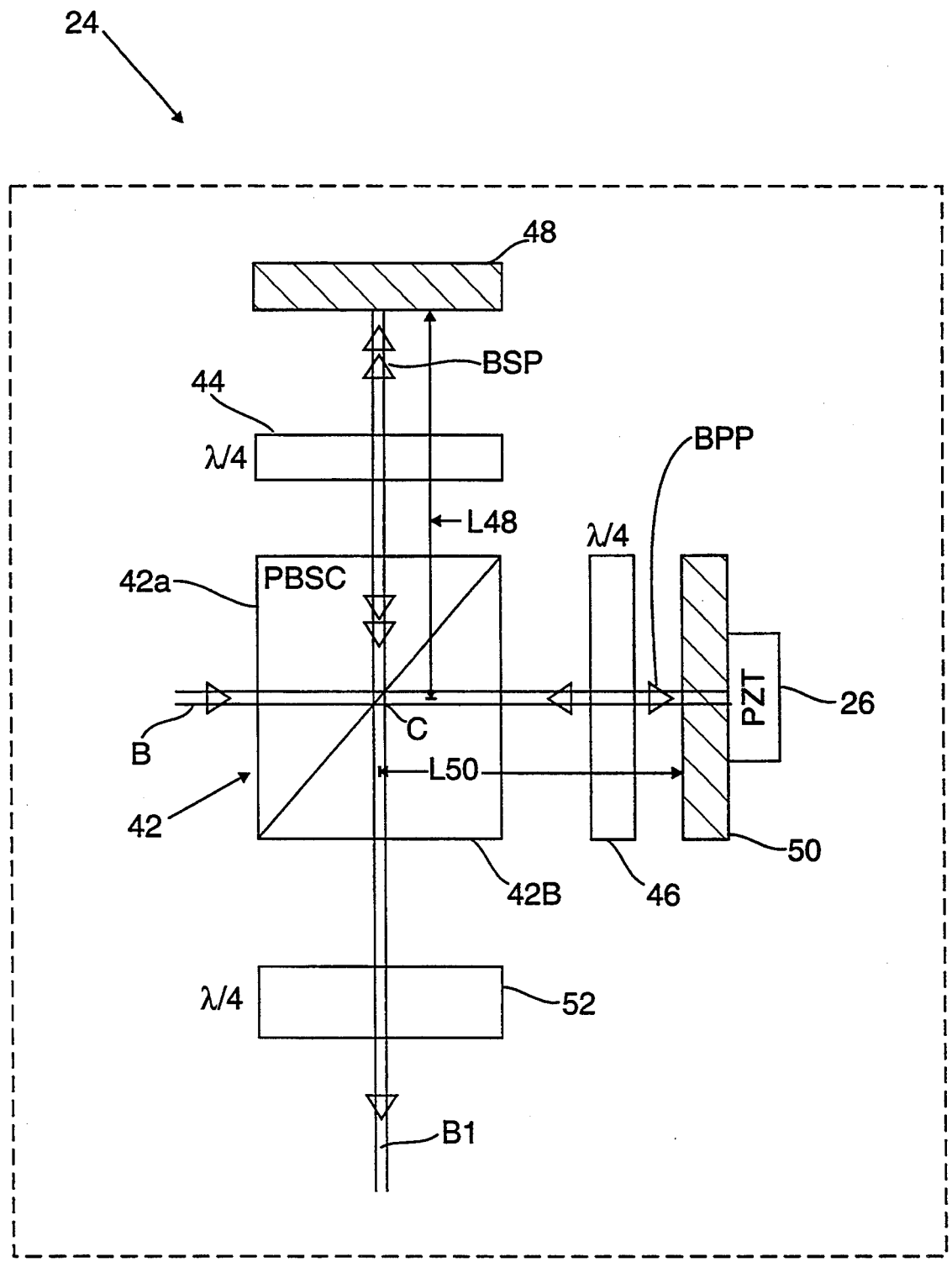
FIG. 2 is a schematic structural view of the polarizing frequency shifter of FIG. 1 for measuring polarization rotation angle.

Referring to FIG. 2, a preferred structure of PFS 24 includes a polarized-beam splitter cube (hereafter referred to as "PBSC") 42 which has an optical beam input side 42a and an optical beam output side 42b. PBSC 42 splits beam B, which can be unpolarized, into two optical beams BSP and BPP, preferably with a 50/50 ratio. Optical beams BSP and BPP are polarized and have orthogonal (mutually perpendicular) directions of polarizations. Optical beam BSP is a so-called S-polarized beam having a polarization direction which is perpendicular to the plane of incidence (i.e., to the plane of the drawing). Optical beam BPP is a so-called P-polarized beam, having a polarization direction which is in the plane of incidence (i.e., in the plane of the drawing).

Located on two adjoining sides of PBSC 42 are quarter-wave plates 44 and 46, respectively. A quarter-wave plate is a well known optical element that introduces a phase delay equal to a quarter of the wavelength and which is characterized by a fast axis and a slow axis. Each quarter-wave plate 44 and 46 has an orientation of the direction of their fast axes so that they form a 45° angle with respect to the polarization direction of optical beams BPP and BSP.

Although in FIG. 2 plates 44 and 46 are illustrated separated from PBSC 42, in the actual construction of PFS 24 they may be cemented or bonded to the respective sides of PBSC 42. Mirrors 48 and 50 are respectively located outwardly of, and spaced distances L48 and L50 from the center C of PBSC 42. The difference between distances L48 and L50 is maintained at a value less than the coherent length of laser diode 22. In order to achieve a desired accuracy on the order of a few millidegrees, it is desirable that the above mentioned distance difference be less than 1.0 mm.

One of the mirrors, e.g., mirror 50, is attached, e.g., cemented to PZT 26. PZT 26 is operated at selected frequency f that is sufficiently high to not be affected by mechanical vibration frequencies, which are typically less than 600 Hz, and sufficiently low to measure a phase shift on the order of ones of millidegrees (e.g., 3 millidegrees). A suitable frequency range is 650 Hz to 15 kHz. A preferred frequency range is selected from between 700 Hz and 5 kHz.

Located on optical beam output side 42B of PBSC 42, is a quarter-wave plate 52 which has its fast axis parallel to that of quarter-wave plate 44. Plate 52 is preferably secured to PBSC 42.

In operation, the S-polarized beam BSP reflects off mirror 48, passes back through center C and exits side 42B of PBSC 42. The P-polarized optical beam BPP reflects off vibrating mirror 50 and becomes phase-modulated, and passes back to center C of PBSC 42 where it is reflected through side 42B and combined with the reflected optical beam BSP. The combined or composite reflected optical beams BSP and BPP then pass through quarter-wave plate 52 to provide polarized-modulated optical beam B1.

Figure 3:
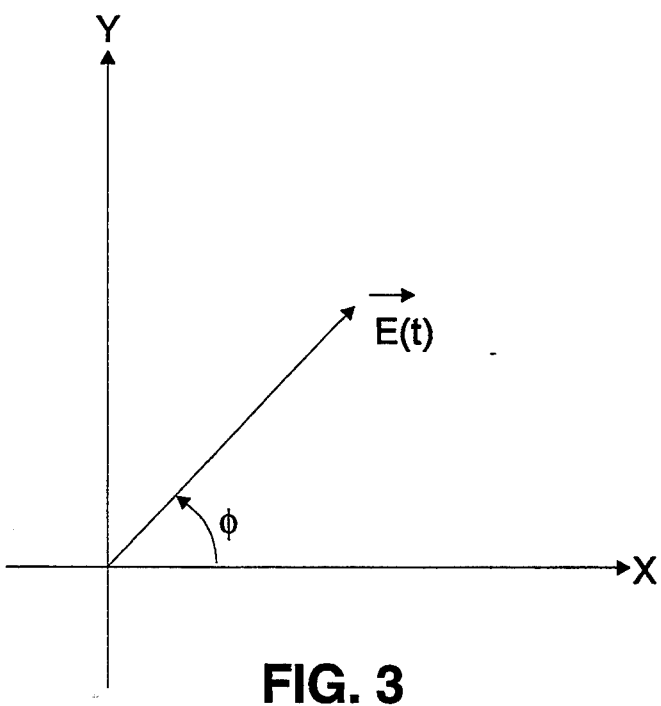
FIG. 3 is a graph illustrating the rotating vector of polarization in the plane of travel.

The output optical beam B1 of PFS 24 is a vector $\bar{E}$ which is defined by an angle $\phi$ and an amplitude $E_o$, as described below, and which is illustrated as beam $\bar{E}(t)$ in FIG. 3. FIG. 3 illustrates an X-Y coordinate system and a vector $\bar{E}$ of polarization which rotates in the plane XY with a frequency f/2. Angle $\phi$ is an angle of rotation of vector $\bar{E}$, which varies with frequency f/2. Angle $\phi$ is determined by the following formula:

$$\bar{E}(t) = E_o \bar{e}(t)$$

$$\bar{e}(t) = \bar{e}_x \cos \phi + \bar{e}_y \sin \phi$$

$$\phi = \phi_o + \pi ft$$

where $\phi_o$ is a constant phase shift caused by the difference in the path lengths L48 and L50 between center C of PBSC 42 and respective mirrors 48 and 50, vector $\bar{e}(t)$ is a single vector of polarization, vectors $\bar{e}_x$ and $\bar{e}_y$ are single coordinate vectors which show the directions of the coordinate axes, and $E_o$ is an amplitude of laser beam B. As will be explained below, the phase of the polarized-modulated optical beam B1, and the phase shift introduced by the glucose concentration, can be recovered by using the reference polarizer 58 (FIG. 4) and the measuring polarizer 68 in the balanced receiver 62 (FIG. 5).

Figure 4:
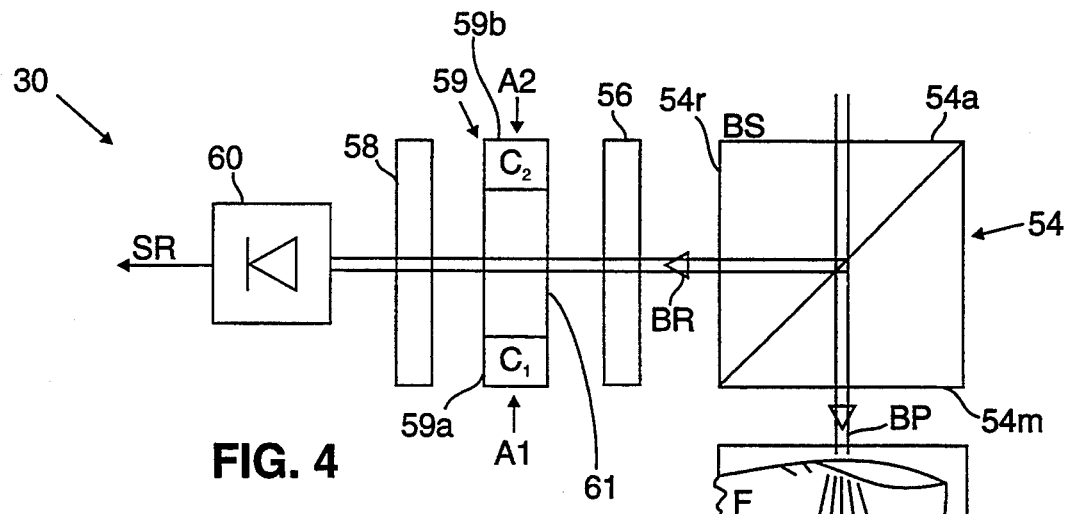
FIGS. 4 is a schematic structural view of the optical transducer of FIG. 1.
Figure 5:
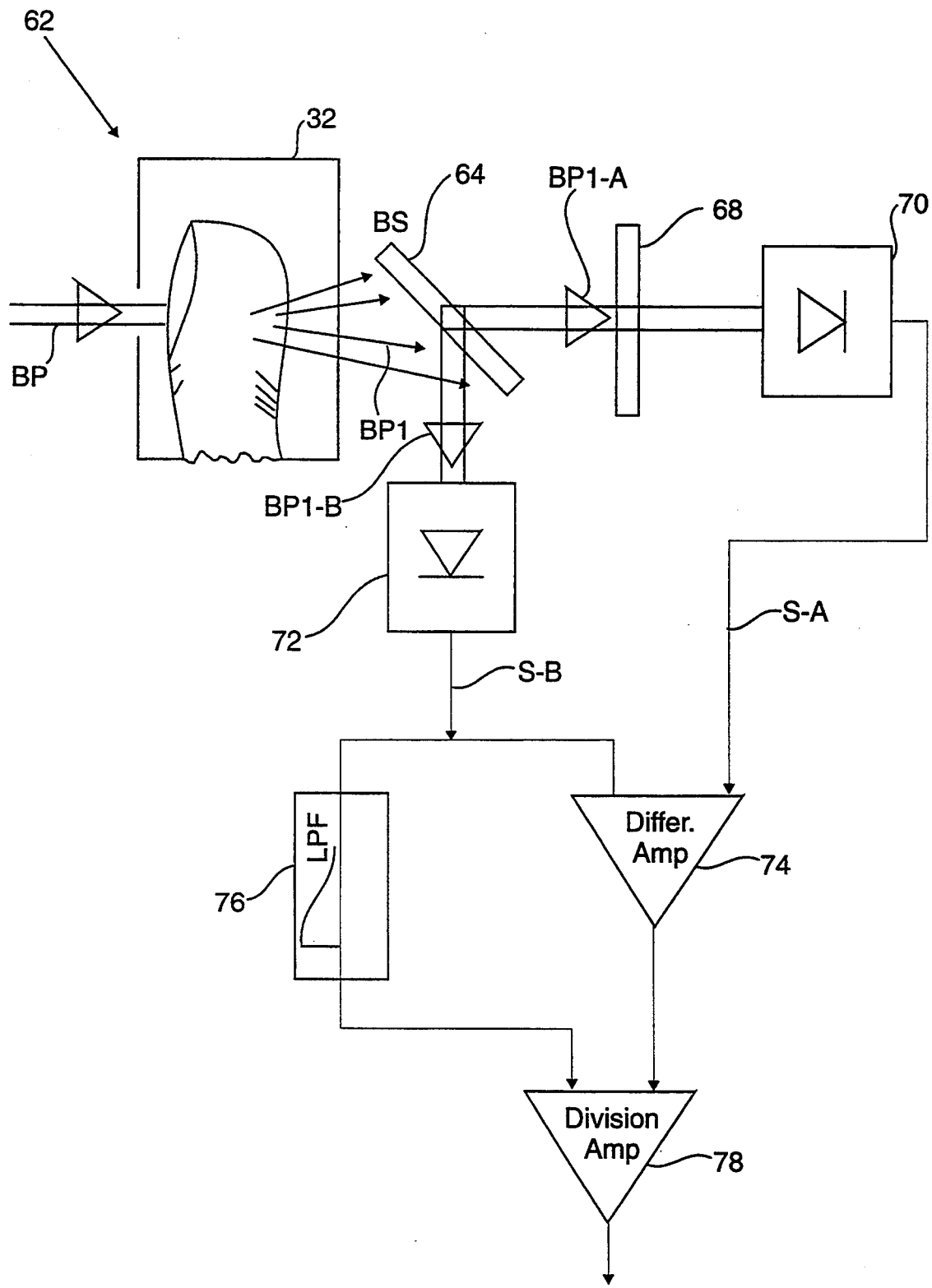
FIG. 5 is a block diagram of the balanced receiver of FIG. 4.

Referring to FIGS. 4, 5, and 6, optical transducer 30 includes an optical beam splitter cube 54 which has an optical beam input side 54a, a reference optical beam output side 54r, and a measurement optical beam output side 54 m. It preferably has a ratio of 50/50, i.e., it is a conventional optical element which splits an input optical beam, namely optical beam B1, into two mutually-perpendicular components, namely optical beams BR and BP with a 50:50 ratio. The one optical beam BR is passed through a reference channel including a neutral-density attenuator 56, a polarizer 58, and a photodetector 60. Attenuator 56, polarizer 58, and photodetector 60 are arranged on an axis with optical beam BR, spaced sequentially from reference optical output side 54r, as illustrated in FIG. 4. In as much as optical beam BR is used to provide a reference phase measurement, its intensity may be attenuated by attenuator 56 to optimize recovery of the phase portion of the optical beam. The attenuation may be on the order of 40–80%. Polarizer 58 is used to recover the reference signal phase information. Photodetector 60 produces electrical signal SR having a phase modulation corresponding to the reference optical beam BR.

A cartridge 59 is placed between attenuator 56 and polarizer 58 for calibration purposes. Cartridge 59 contains two reference cells 59a and 59b and a transparent window 61. Cell 59a contains a first concentration $C_1$ of a glucose solution and cell 59b contains a second concentration $C_2$ of a glucose solution. Each cell has an equal optical pathlength (i.e., the length through which optical beam BR passes), e.g., 1.0 cm. Window 61 has the same construction as cells 59a and 59b except that it is empty. Alternatively, window 61 may be an aperture.

Figure 4A:
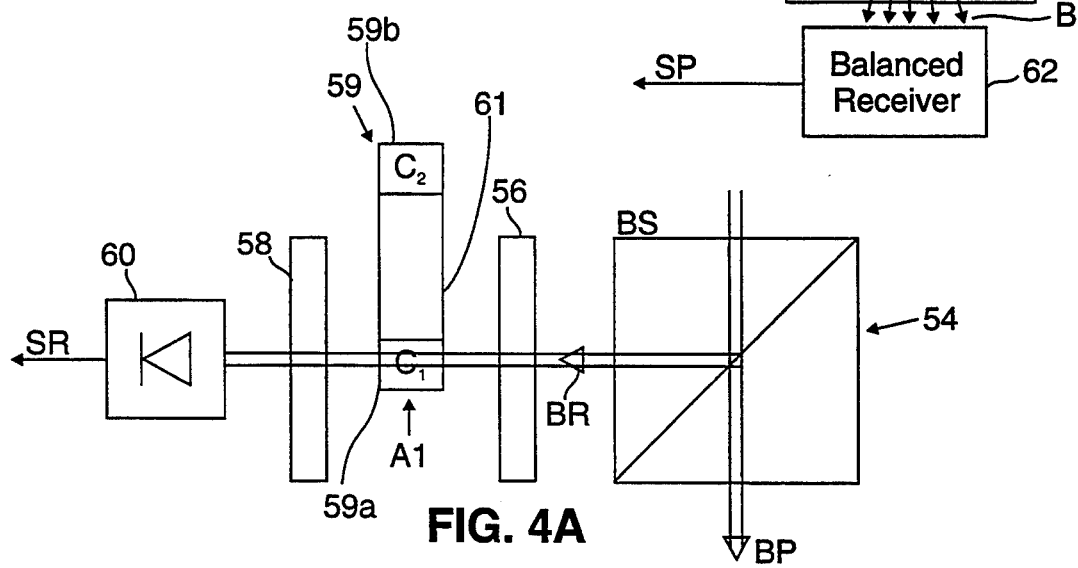
FIGS. 4A and 4B are partial structural views of FIG. 4 showing the calibration cell cartridge in different positions.
Figure 4B:
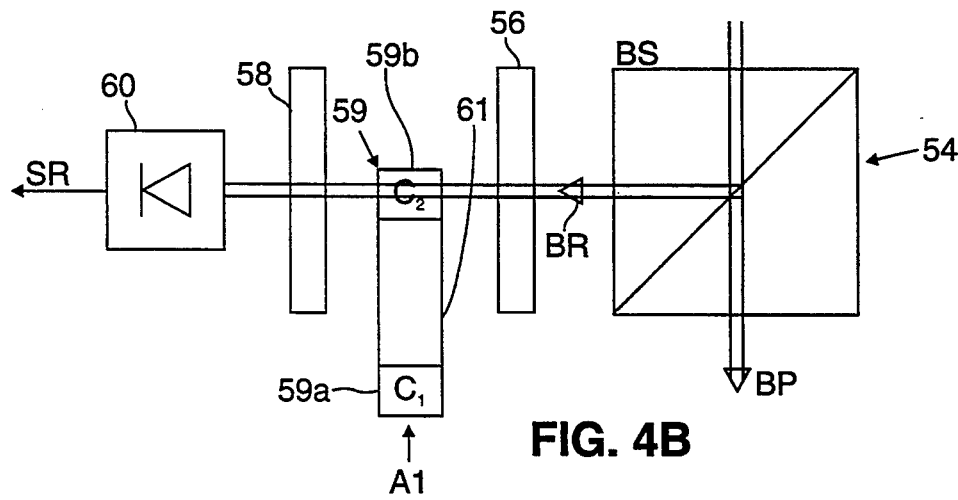

In this embodiment, cell 59a, transparent window 61, and cell 59b are linearly arranged on a sliding structure with window 61 located between cells 59a and 59b. Cartridge 59 may be shifted from the "central" position, illustrated in FIG. 4, in the direction of either arrow $A_1$ or arrow $A_2$ to the positions respectively shown in FIGS. 4A and 4B. The movement may be manual or automatic under control of microcontroller 116. In FIG. 4, cartridge 59 is in the central position and optical beam BR passes through window 61. In FIG. 4A, cartridge 59 is shifted so that optical beam BR passes through cell 59a. In FIG. 4B, cartridge 59 is shifted so that optical beam BR passes through cell 59b. It should be understood that other configurations for window 61 and cells 59a and 59b could be used, e.g., cells and window spaced about an axis so that cartridge 59 can be rotated from one position to the next.

The other optical beam, probe optical beam BP, is passed through glucose measuring head 32 to balance receiver 62, which are sequentially located on measurement optical output side 54m of beam splitter cube 54. Probe optical beam BP is passed through the glucose measuring head 32 which may contain the object being measured, e.g., a blood carrying body part (tissue) such as a patient's finger F and produces a passed probe optical beam illustrated in FIGS. 4 and 5 as beam BP1. Optical beam BP1 contains a polarized component which carries phase shift information related to the glucose concentration and a depolarized scatter component which does not carry such glucose related information. These components are collectively illustrated as optical beam BP1 in FIG. 5. More specifically, the transmission of optical beam BP through blood-carrying body F changes the direction of polarization of optical beam BP. This introduces a phase shift $\Theta_M$ with respect to reference optical beam BR. Furthermore, the transmission of optical beam BP through finger F is accompanied by the depolarization of part of optical beam BP, which is caused by the scattering of the optical beam in the finger. The depolarized component of optical beam BP1 has a time-constant average intensity and does not contain any information about the phase shift. Therefore, this component of the passed optical beam contributes only to the noise level of the signal. Typically, less than 5% of optical beam BP1 remains polarized after passage through the blood-carrying body. However, because only the polarized component of optical beam BP1 produces an AC signal, that remaining 5% is sufficient data and may be used to recover the polarized signal.

Balanced receiver 62 functions to subtract out electronically the depolarized portion of the optical signal and to leave only the polarized component. It has as its output a probe electric signal SP corresponding to the polarized component of passed probe optical beam BP1.

The structure of a balanced receiver 62 in accordance with a preferred embodiment of the invention is shown in FIG. 5. Receiver 62 includes a beam-splitter plate 64 with a 50:50 splitting ratio. Beam splitter plate 64 receives passed probe optical beam BP1 and divides optical beam BP1 into two equal components BP1-A and BP1-B. One of these components is converted into a polarized component. In this regard, located on the path of optical beam component BP1-A are a polarizer 68 and a photodetector 70. The other component is used as a depolarized component. In this regard, located on the path of optical beam BP1-B is a photodetector 72. Photodetectors 70 and 72 are preferably identical and matched and produce polarized component electric signal S-A and depolarized component electric signal S-B on their respective outputs. Electrical signal S-A also is referred to as the polarized electric component. Electric signal S-B also is referred to as the depolarized electric component.

Balanced receiver 62 also includes a difference amplifier 74, a low-pass filter 76, and a division amplifier 78. Output electric signals S-A and S-B of photodetectors 70 and 72 are directed to the inputs of difference amplifier 74. The output of difference amplifier 74 is connected to an input of division amplifier 78. Low-pass filter 76 is located between photodetector 72 and division amplifier 78 and passes the DC signal components of signal S-B. The other input to division amplifier 78 is the low pass filtered output of photodetector 72. The signal SP output of division amplifier 78 is the ratio of its inputs and provides probe electric signal SP.

One embodiment of the structure of glucose measuring head 32, in which an object, such as finger F, is inserted into an object-receiving recess, is shown in FIG. 6. Unit 32 includes a housing 80 which has a central cavity 82, a spring-loaded axial stop element 84, a side opening 85, and a spring-loaded pressure element 88 having a compression spring 86. Housing 80 also has a second side opening 90 that is closed with a glass plate 92. Central cavity 82 serves to receive a finger F as a measuring object. Opening 90 serves for directing optical beam BP onto a nail bed NB of finger F. Axial stop element 84 serves to adjust the position of finger F so that optical beam BP intersects nail bed NB. Pressure element 88 is intended for the fixation of finger F during measurement and for increasing the amount of blood in the measured portion of finger F. An increase in the amount of blood in the measured portion of finger F reduces the scattering of the light transmitted through finger F and increases the signal-to-noise ratio of the measurement.

On the side of finger F opposite to nail bed NB of finger F, housing 80 has a recess 94 accommodating balance receiver 62. Beam-splitter plate 64 of balance receiver 62 is located on the side of finger F opposite to nail bed NB, i.e., on the side of digital pulp DP of finger F. Beam-splitter plate 64 is protected by a glass plate 96.

Recess 94 also contains a sensor 98 which determines the thickness of finger F in the portion being measured and which generates the above-mentioned signal SL. Sensor 90 may be a capacity-type or a resistor-type sensor capable of determining variations in the capacity or in the resistance between the conditions as they are in the absence of finger F and once finger F has been inserted.

Referring to FIG. 6A, another embodiment of glucose measuring head 32A is shown. This embodiment is located remotely from optical transducer 30 and is connected to it through a polarization-preserving fiber-optical link 100. In this case, a ferrule 102 is inserted into side opening 90 and supports a GRIN rod microlens ("GRIN lens") 104. GRIN lens 104 is a gradient index lens which has an index of refraction which varies in a predetermined relationship with the thickness of the lens. It is intended to produce an output optical beam BP in a collimated form at the output of optical fiber 100. This is used because optical beam BP loses its collimation properties when it is transmitted through optical fiber 100. Polarization preserving optical fibers and GRIN lenses are commercially available products. The remaining parts of unit 32A are the same as those of unit 32 shown in FIG. 6.

Referring to FIG. 6B, an embodiment of glucose measuring head 32B for using a patient's earlobe E as the blood-carrying body is shown. In this embodiment, glucose measuring head 32B is attached to a head appliance 106 such as an arc-shaped head holder or band or a head band or of the same type as are used in conventional head sets including earphones for supporting microphones on the head of a wearer. Head appliance 106 supports a speaker/microphone 35 for reproducing audio information about the glucose concentration, which is provided by suitable circuitry (not shown) associated with signal processing unit 34. Preferably, speaker/microphone 35 is supported at one end of head appliance 106. Head appliance 106 also supports a U-shaped clip 101 which, in turn, supports glucose measuring head 32b and which can be attached to earlobe E of the patient. One side of clip 101 holds a GRIN rod lens 104b with an optical fiber link 100b while the other side of clip 101 holds a balance receiver 62 with a thickness sensor (not shown). Structurally, GRIN rod lens 104b, balance receiver 62, and the sensor of the embodiment of FIG. 6B may be the same as those of FIG. 6a.

Figure 7:
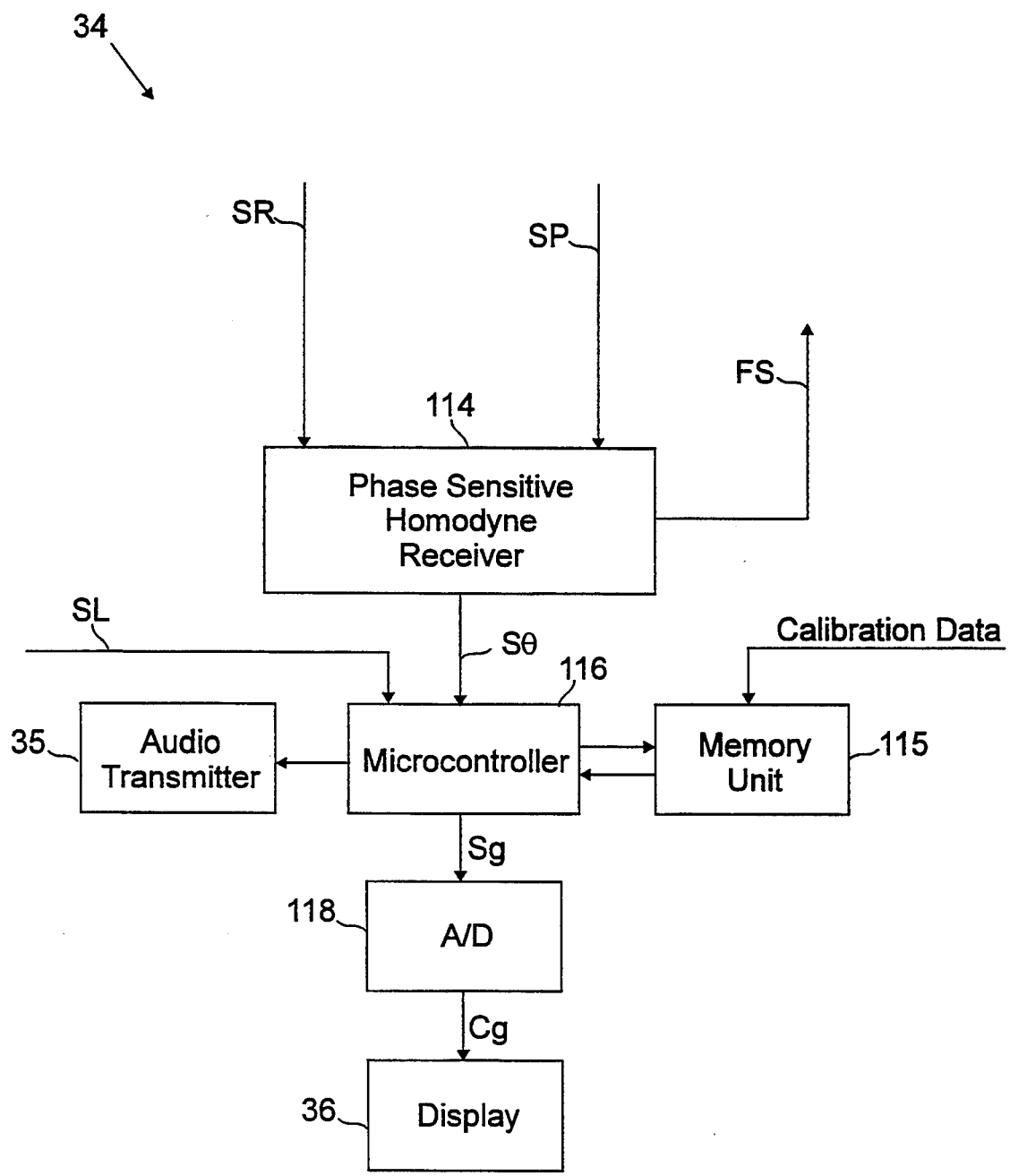
FIG. 7 is a block diagram of the electronic signal processing unit of FIG. 1.

Referring to FIG. 7, electronic signal processing unit 34 includes a phase-sensitive homodyne receiver 114, which receives the reference electric signal SR and the probe electric signal SP and produces on its output an electric signal $S\Theta$ which is proportional to a blood glucose concentration, a microcontroller 116, which processes signal $S\Theta$ in order to convert it into a glucose-concentration signal $S_G$, and an analog-digital (A/D) converter 118 which receives, e.g., signal $S_G$ and converts it into digital information $C_G$. The output of A/D converter 118 is passed to display 36 for displaying the obtained information about the concentration of glucose in the blood.

Phase-sensitive homodyne receiver 114 is a device which determines the phase difference between signals SR and SP. It may operate based on either a lock-in amplifier technique or a time-interval counter operating in a phase mode, in accordance with conventional techniques. One useful phase-sensitive homodyne receiver, with a resolution of 0.001° in phase difference, is available from Stanford Research Systems, Inc., Sunnyvale, Calif.

Electronic signal processing unit 34 also contains a memory unit 115 which is connected to microcontroller 116 and which may store data required for custom calibration of apparatus 20, patient's measurement data, etc.

In order to exclude the effect of statical phase shift $\Theta_o$, which may occur because of temperature (ambient or sample) variations, misalignment in the optical system, imperfect optics (designed not exactly for the given wavelength), etc., each measurement procedure preferably begins with calibration of apparatus 20. For this purpose, prior to actual measurement on the object, a reference calibration procedure is carried out by first passing optical beam BR through transparent window 61 (FIG. 4) and then sequentially through cells 59a and 59b. Ideally, the calibration procedure using cells 59a and 59b can be omitted. However, for manufacturability and use over long periods of time, e.g., months and years, frequent calibration is desired for continued accuracy.

For the calibration, cells 59a and 59b are sequentially shifted (in any order) into the positions shown in FIGS. 4A and 4B in which they alternatively interfere with the optical path of optical beam BR. The calibration procedure is the same as measuring the glucose concentration in object F, except that no tissue is inserted in measuring head 32, the meanings of signals SR and SP are reversed, and signal SL is not used because the sample cell path length is known, i.e., 1 cm. The details of the propagation of the optical beams and processing of the obtained information is discussed below with reference to the measurement of glucose in blood carrying body part F.

Figure 8:
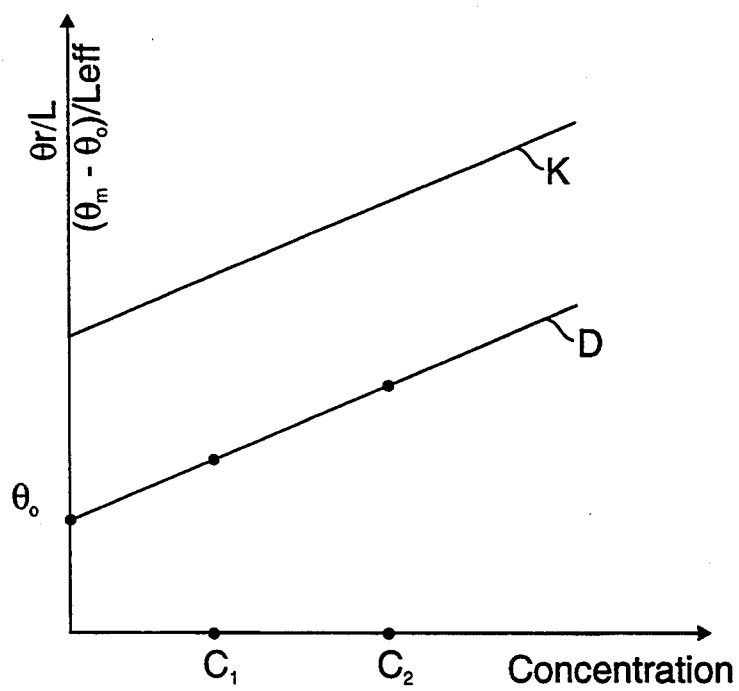
FIG. 8 is a graph illustrating a calibration procedure.

Both cells 59a and 59b contain glucose solution samples of different known glucose concentrations $C_1$ and $C_2$. The results of the calibration measurement will thus produce two points in a relationship between a reference phase difference $\Theta_R$ (per 1 cm of the pathlength) and glucose concentration $C_G$. This is shown in FIG. 8. The results of the calibration are shown by the curve labelled D in FIG. 8. From this reference calibration, one can obtain statical phase shift $\Theta_o$ per 1 cm of pathlength. It should be understood that cells 59a and 59b alternatively may contain or comprise some optically active material (in any state), other than two different solutions of glucose, which have the same effects on the polarized-modulated laser beam as do the glucose solutions at two different known concentrations, but have a longer useful life than solutions of glucose.

In measuring tissue F, however, the phase shift $\Theta_M$ between probe electric signal SP and reference electric signal SR will depend on many factors, including effective pathlength $L_{EFF}$ for beam BP. Effective length $L_{EFF}$ is only that part of the optical path of beam BP which is passed only through the blood-filled portion of the measurement object and differs from actual thickness of the finger. Therefore, in order to obtain the glucose-concentration information from the results of measurement, it is necessary to subtract all extraneous data.

Phase shift $\Theta_M$ may be generally expressed by the following formula (1):

$$\Theta_M = \alpha_{GL} C_{GL} L_{EFF} + \Theta_{SUB} + \Theta_o \tag{1}$$

where $\Theta_{SUB}$ is a phase shift introduced by other blood components which also are optically active, i.e., subject to optical rotation at the wavelength of light used, and $\alpha_{GL}$ is a known optical parameter which, for a given wavelength, may be obtained from spectroscopy data.

Each subject, however, has $\Theta_{SUB}$ which is constant in time and does not depend on the changes in the glucose concentration. This parameter and effective path-length $L_{EFF}$ may be obtained based on two (or more) measurements taken at different glucose concentrations for which the glucose concentrations are obtained by a conventional invasive procedure (e.g., a finger poke measurement, laboratory analysis, or other biochemical analysis method, preferably on the basis of finger poke measurements). For this purpose, the concentration of glucose is measured at least twice: for example, once on an empty stomach and once an hour after administration of a concentrated solution of dextrose (or any other substance which raises the blood glucose level). These calibrating measurements need be performed only once for each person, prior to using the apparatus for the first time, as part of a start-up calibration procedure. The results of such two calibrating measurements may be expressed by the following formulae (2.1) and (2.2):

$$\Theta_{M1} = \alpha_{GL} C_{GL1} L_{EFF} + \Theta_{SUB} + \Theta_o \tag{2.1}$$

$$\Theta_{M2} = \alpha_{GL} C_{GL2} L_{EFF} + \Theta_{SUB} + \Theta_o \tag{2.2}$$

where $C_{GL1}$ and $C_{GL2}$ are the measured concentrations of glucose and $\Theta_{M1}$ and $\Theta_{M2}$ are the phase shifts measured by apparatus 20 at approximately the same time that the two glucose samples are obtained, respectively. These values are introduced into and stored in memory unit 115. The more calibration measurements that are made during the one-time start-up calibration procedure, the more accurate the calibration information will be.

From formulae (2.1) and (2.2), effective length $L_{EFF}$ can be expressed as follows:

$$L_{EFF} = \frac{\Theta_{M2} - \Theta_{M1}}{\alpha_{GL}(C_{GL2} - C_{GL1})} \quad (3)$$

Substituting formulas (3) into (1), a general expression for $\Theta_M$ is obtained as follows:

$$\Theta_M = \frac{C_{GL}(\Theta_{M2} - \Theta_{M1})}{(C_{GL2} - C_{GL1})} + \Theta_{SUB} + \Theta_O \quad (4)$$

Now the curve corresponding to formula (4) should be compared with reference calibration curve D. In order to ensure meaningful comparison, both curves must be normalized against the pathlength, i.e., each curve is divided by its pathlength.

FIG. 8 shows the normalized curve D and curve K. For curve D, the ordinate represents $\Theta_R/L$ (L=1 cm). For curve K, the ordinate represents $(\Theta_M-\Theta_o)/L_{EFF}$. Theoretically, both curves are parallel and represented by straight lines. In reality, however, they may have some deviations from the theoretical condition. Accordingly, memory unit 115 contains a suitable algorithm, which can be derived from experimentally acquired data, for processing the above-mentioned data by known methods of correlation analysis so as to minimize the above-mentioned deviations. One of the variables of such algorithm may be an actual thickness of the finger. It is understood that the above formulae are parts of the algorithm and that all calculations are performed automatically in microcontroller 116. Upon completion of the calibration procedures, including the one-time start-up calibration, apparatus 20 is ready for actual measurement.

Operation of apparatus 20 of the invention for measuring the blood-glucose concentration will be now described for the case of glucose measuring head 32 for a finger F built into the apparatus (i.e., for non-remote version of FIGS. 4 and 6).

When apparatus 20 is switched on, laser diode 22 generates a laser beam B which is directed through collimating lens 40 to PFS 24. PFS 24 produces a polarization modulation of optical beam B via mirror 50 and PZT 26 which is driven by piezoelectric controller 28. The resulting polarized-modulated optical beam B1 is sent to optical transducer 30. Optical transducer 30 splits optical beam B1 into a polarized-modulated reference optical beam BR and a polarized-modulated probe optical beam BP. Reference optical beam BR is passed through optical attenuator 56, window 61, polarizer 58, and converted by photodetector 60 into reference electric signal SR. Probe optical beam BP is sent to glucose measuring head 32.

For measuring the blood glucose level, the patient inserts his/her finger F into opening 82 against spring-loaded stop element 84 and adjusts the position of finger F so that nail bed NB is aligned with the position of side opening 90. At the same time, spring-loaded pressure element 88 applies pressure to finger F behind the measurement portion, whereby the amount of blood in the finger flesh to be measured increases to increase the sensitivity of measurements.

Probe optical beam BP thus passes through the blood of finger F and becomes passed probe optical beam BP1. Transmission of probe optical beam BP through finger F changes the direction of polarization of the resulting optical beam BP1 because glucose is an optically active material for the wavelength of probe optical beam BP. This introduces a phase shift $\Theta_M$ for optical beam BP1 with respect to reference optical beam BR. For a wavelength $\lambda=850$ nm and a blood glucose concentration of 70 mg/100 ml, the phase shift is on the order of 4.7 millidegrees.

The transmitted optical beam BP1 passes through protective plate 96 to a beam-splitting plate 64 of balanced receiver 62. In balanced receiver 62, optical beam BP1 is split into two optical beams BP1-A and BP1-B. Component BP1-A is directed through polarizer 68 to photodetector 70. Photodetector 70 produces an electrical signal S-A corresponding to the polarized component of optical beam BP1-A, which is input to difference amplifier 74. At the same time, component BP1-B is directly passed to photodetector 72. Photodetector 72 produces an electric signal S-B corresponding to the non-polarized component of optical beam BP1-B, which is also input to difference amplifier 74.

Difference amplifier 74 then provides an output that is the difference between the electrical signals S-A and S-B corresponding to depolarized and polarized components of optical beams BP1-A and BP1-B. The output signal of difference amplifier 74 thus carries information only about the polarized component BP1-A. However, the amplitude of this difference signal still contains noise associated with light scattering. To further reduce this noise component, the amplitude of the output signal from difference amplifier 74 is divided, in division amplifier 78, by the amplitude of the signal from photodetector 72 which contains the same scattering noise. More specifically, the output of photodetector 72 is passed through low-pass filter 76 for removing frequencies above 10 to 100 Hz and the filtered signal is provided as the denominator to the division amplifier 78. The resulting probe electric signal SP thus carries information about polarized component BP1-A, but the amplitude of signal SP is free of the noise influence.

Reference electric signal SR and probe electric signal SP are then passed to phase-sensitive homodyne receiver 114. An output of homodyne receiver 114 is provided as a feedback signal FS to piezoelectric controller 28. Receiver 114 extracts a phase-difference signal $S\theta$, which is sent to the input of microcontroller 116. At the same time, microcontroller 116 receives length measurement signal SL from sensor 98 and calibration data from memory unit 115.

On the basis of the algorithm, phase difference signal $S\theta$, length signal SL, and calibration data, microcontroller 116 produces a signal $S_G$ proportional to the concentration of glucose. Signal $S_G$ is converted by A/D converter 118 into a digital glucose-concentration information $C_G$ which can be shown on display 36 and/or indicated on display 35. The apparatus uses averaging techniques for the measurements to extract the best signal to noise information and may require up to a minute to produce a glucose concentration measurement. Averaging will average out variations in blood volume due to pulsatile blood flow, motion artifact and other movements.

Apparatus 20 made in accordance with the embodiment of the remotely located glucose measuring head shown in FIG. 6A operates in the same manner as the apparatus of the embodiment of FIG. 6 except that optical beam BP is transmitted to finger F or another blood-carrying part, via optical-fiber link 100 and GRIN lens 104.

In the case of apparatus 20 made in accordance with the embodiment of glucose measuring head 32B shown in FIG. 6B, head appliance 106 is put on the patient's head as in the case of a conventional headphone so that transducer 108 is located near one ear of the wearer while the lobule E of the other ear of the patient is clamped by clip 101. In this manner, ear lobule E is located on the optical path of optical beam BP between fiber-optical link 100b and balanced receiver 62b. All other parts operate on the same principle as similar parts of the previous embodiment.

In an actual construction, apparatus 20 may have small dimensions of about 40 cm×15 cm×20 cm, or less. This allows the use of the apparatus as a home and portable monitoring device. Use of customizable ASIC devices and/or customized integrated circuits will permit reducing the size further. A rechargeable battery (or replaceable battery) may be used to operate the system electronics to permit portable use.

The embodiments described above in connection with FIGS. 1 through 8 relate to a method and apparatus based on the measurement of a polarization rotation angle of light transmitted through in vivo tissue. The above described method and apparatus are based in part on an assumption that dependence of an angle of rotation on a wavelength has a maximum and that in a preferred embodiment of the apparatus the operative wavelength corresponds to this particular maximum.

It is known, however, that any optically active medium, e.g., glucose, may interact with an incident polarized light in two different ways. In other words, the above medium may either change the angle polarization of the linear component of the polarized incident light, or (if the incident light contains left and right circular polarized components) it may absorb the left and right circular polarized components differently. The latter one is known as "circular dichroism".

Another aspect of the present invention concerns an apparatus for determining blood-glucose concentration by measuring circular dichroism. In general, the apparatus is the same as the one described above with reference to FIGS. 1 through 8. The main difference between both embodiments is in the structure of the polarizing frequency shifters. Therefore, in the following description of the apparatus based on measurement of circular dichroism, only those components and elements which are different will be described in detail. Furthermore, in the drawings of FIGS. 9 and 10 the portions of the second embodiment having parts identical with the first embodiment will be designated by the same reference numerals with an addition of 100.

Figure 9:
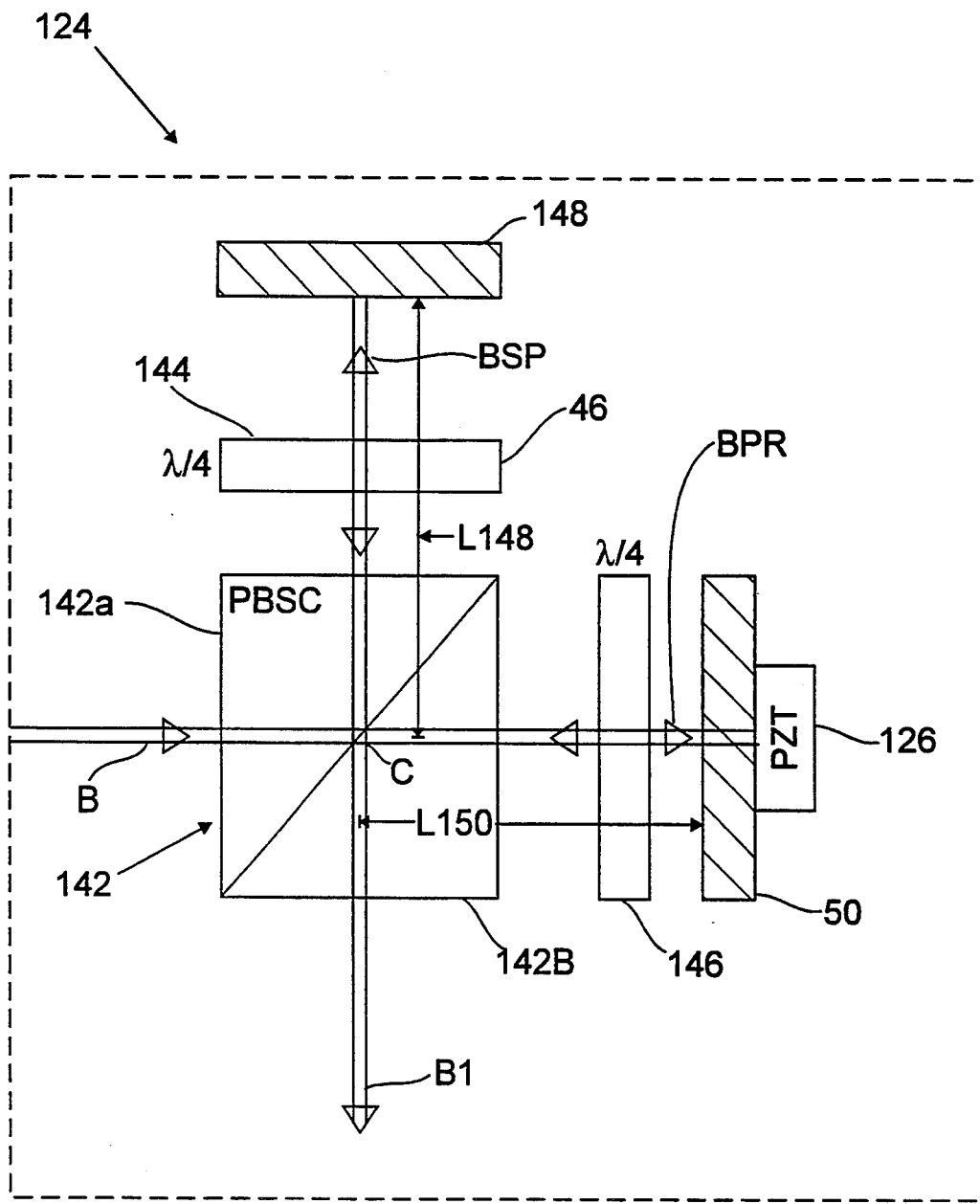
FIG. 9 is a schematic structural view of the polarizing frequency shifter in accordance with a second embodiment of the present invention.

Referring to FIG. 9, a polarizing frequency shifter 142 for measuring circular dichroism is shown. Polarizing frequency shifter of FIG. 9 is identical to polarizing frequency shifter 42 of FIG. 2, with the exception that shifter 142 does not have output quarter-wave plate 52.

Figure 10:
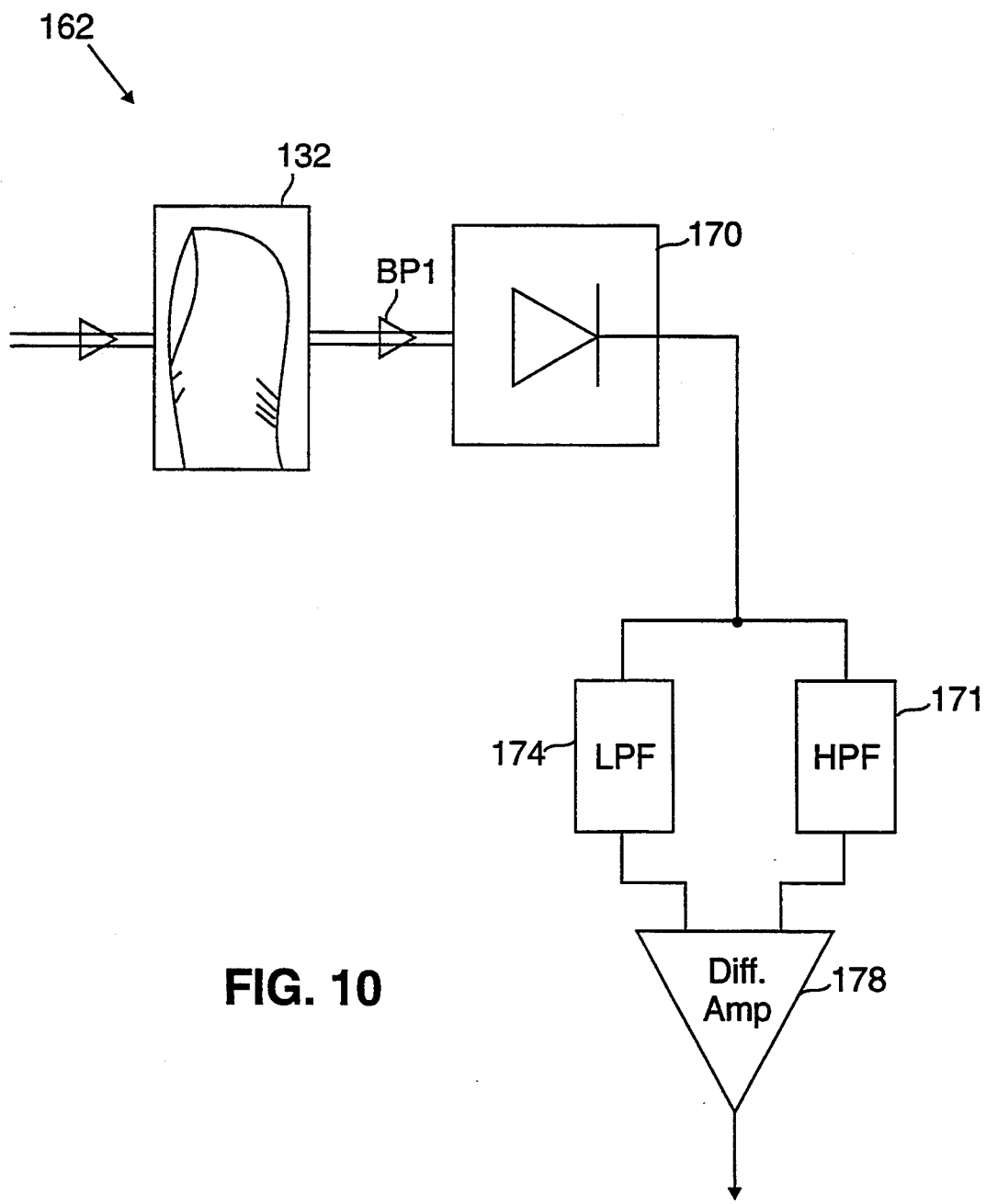
FIG. 10 is a block diagram of the balanced receiver for operation in conjunction with polarizing frequency shifter of FIG. 9.

Similarly, FIG. 10 shows a block diagram of a photoreceiver 162 of FIG. 4 which is suitable for the embodiment of the shifter of FIG. 9. The parts identical with those of FIG. 5 will be designated by the same reference numerals, but with an addition of 100.

Receiver 162 includes a photodiode 170 which receives probe optical beam BP1 and converts it into a mixture of DC and AC electrical signals. An output of photodiode 170 is connected to a division amplifier 178 via a low-pass filter 174 and a high-pass filter 171 which are connected in parallel to each other. An output of division amplifier 178 is an AC signal $S_{out}$ which may be represented by the following a formula:

$$S_{out} = (A_{RCD} - A_{LCD}) \sin(2\pi ft + \phi_o),$$

where $(A_{RCD} - A_{LCD}) = C_{GL}(\alpha_{RCD} - \alpha_{LCD})/\alpha_o$, where $\alpha_{RCD}$ and $\alpha_{LCD}$ are absorption coefficients for right and left circular polarized lights, and $\alpha_o$ is an absorption coefficient for a non-polarized light.

Operation of the apparatus for measuring glucose concentration on the principle of circular dichroism will now be described with reference to the drawings of the previous embodiment, with the exception that FIG. 2 and 5 will be replaced by FIGS. 9 and 10.

When apparatus 20 is switched on, laser diode 22 generates a laser beam B which is directed through collimating lens 40 to PFS 124 (FIG. 9). PFS 124 produces a polarization modulation of optical beam B via mirror 150 and PZT 126 which is driven by piezoelectric controller 28. The resulting polarized-modulated optical beam B1 constitutes a 50%:50% mixture of left and right circular polarized beams, which may be expressed as follows:

$$\bar{E}_{B1} = \bar{E}_{RCP}(1 - ie^{i2\pi ft + i\phi_o}) + \bar{E}_{LCP}(1 + ie^{i2\pi ft + i\phi_o})$$

where $E_{RCP}$ is the amplitude of the right circular polarized component of beam B1, $E_{LCP}$ is the amplitude of the left circular polarized component of beam B1, and $E_{B1}$ is the amplitude of beam B1; $\phi_o$ and f are the same as defined in the first embodiment.

Optical transducer 30 splits optical beam B1 into a polarized-modulated reference optical beam BR and a polarized-modulated probe optical beam BP. Reference optical beam BR is passed through optical attenuator 56, window 61, polarizer 58, and converted by photodetector 60 into reference electric signal SR. Probe optical beam BP is sent to glucose measuring head 32.

For measuring the blood glucose level, the patient inserts his/her finger F into opening 82 against spring-loaded stop element 84 and adjusts the position of finger F so that nail bed NB is aligned with the position of side opening 90. At the same time, spring-loaded pressure element 88 applies pressure to finger F behind the measurement portion, whereby the amount of blood in the finger flesh to be measured increases to increase the sensitivity of measurements.

Probe optical beam BP thus passes through the blood of finger F and becomes passed probe optical beam BP1. Transmission of probe optical beam BP through finger F changes the direction of polarization of the resulting optical beam BP1 because glucose is an optically active material for the wavelength of probe optical beam BP. As a result, an absorption difference occurs between the left and right circular polarized components of the incident light. For a wavelength $\lambda = 850$ nm and a blood glucose concentration of 70 mg/100 ml, the absorption difference is on the order of $(2 \text{ to } 5) \times 10^{-5}$.

The transmitted optical beam BP1 passes through protective plate 96 to a photodiode 170. The output signal of photodiode 160 is sent via parallel filters 171 and 174 to division amplifier 178 which produces on its output an AC signal $S_{out}$. The output signal $S_{out}$, which carries information only about circular dichroism caused by glucose absorption of the light, constitutes a probe electrical signal SP.

Reference electric signal SR and probe electric signal SP are then passed to phase-sensitive homodyne receiver 114. An output of homodyne receiver 114 is provided as a feedback signal FS to piezoelectric controller 28. Receiver 114 extracts the amplitude of probe electrical signal SP, which is sent to the input of microcontroller 116. At the same time, microcontroller 116 receives length measurement signal SL from sensor 98 and calibration data from memory unit 115.

The signals are finally processed in a manner similar to the apparatus of the first embodiment.

Embodiment of Apparatus with Frequency Modulation of Laser Diode

The first and second embodiments of the apparatus described above with reference to FIGS. 1 through 10 related to phase modulation of a laser beam by passing it through PFSs 24 and 124 based on the use of piezoelectric transducers 26 and 126, respectively. Depending on the costs requirements and characteristics (power, wavelength, and spectral width) of the laser source used in the apparatus, it may appear more advantageous to utilize direct frequency modulation of laser diode 22, instead of the use of piezo movements of PFS 24.

Figure 11:
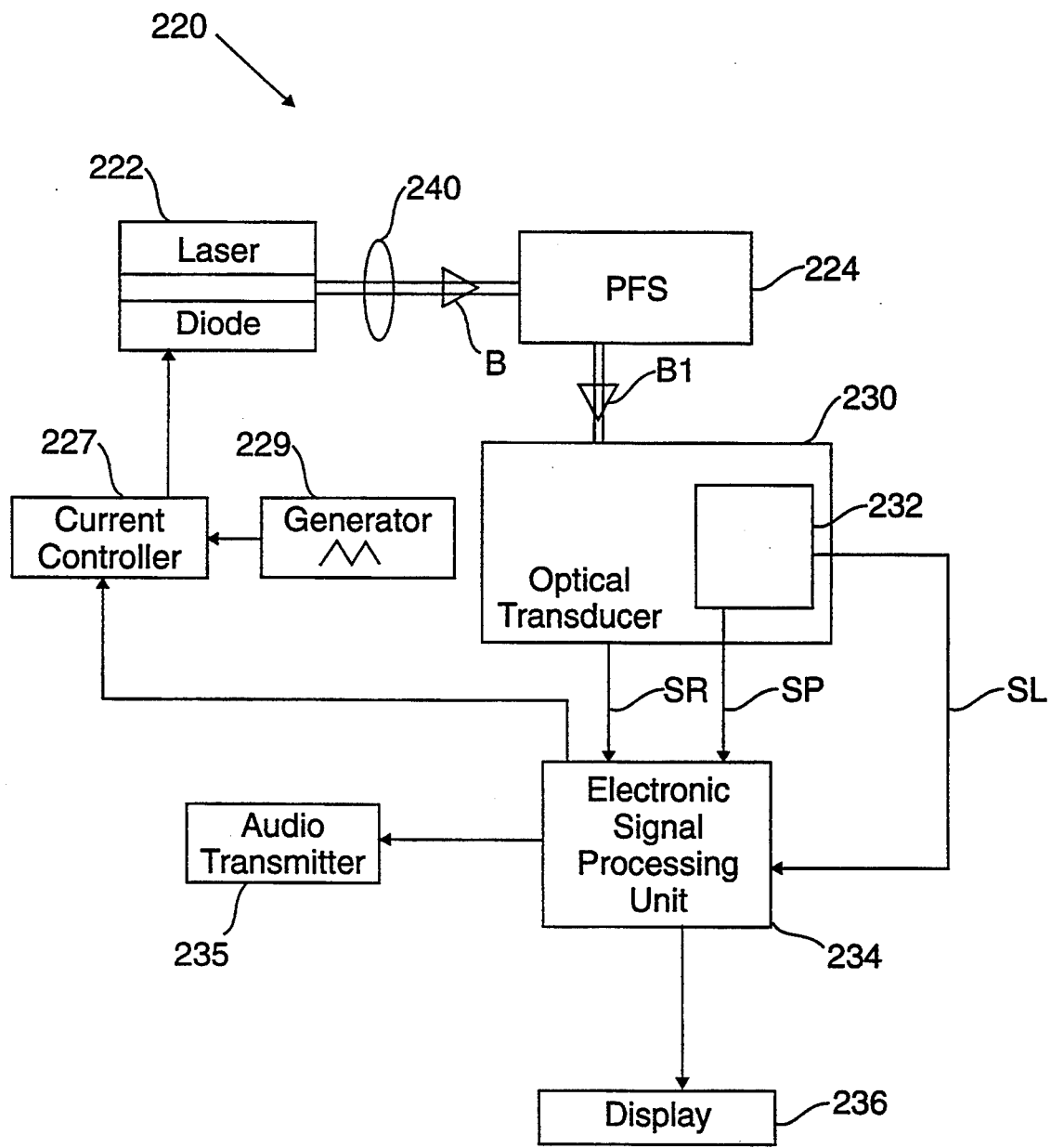
FIG. 11 is a block diagram of a third embodiment of the present invention utilizing direct frequency modulation of a laser diode.
Figure 12:
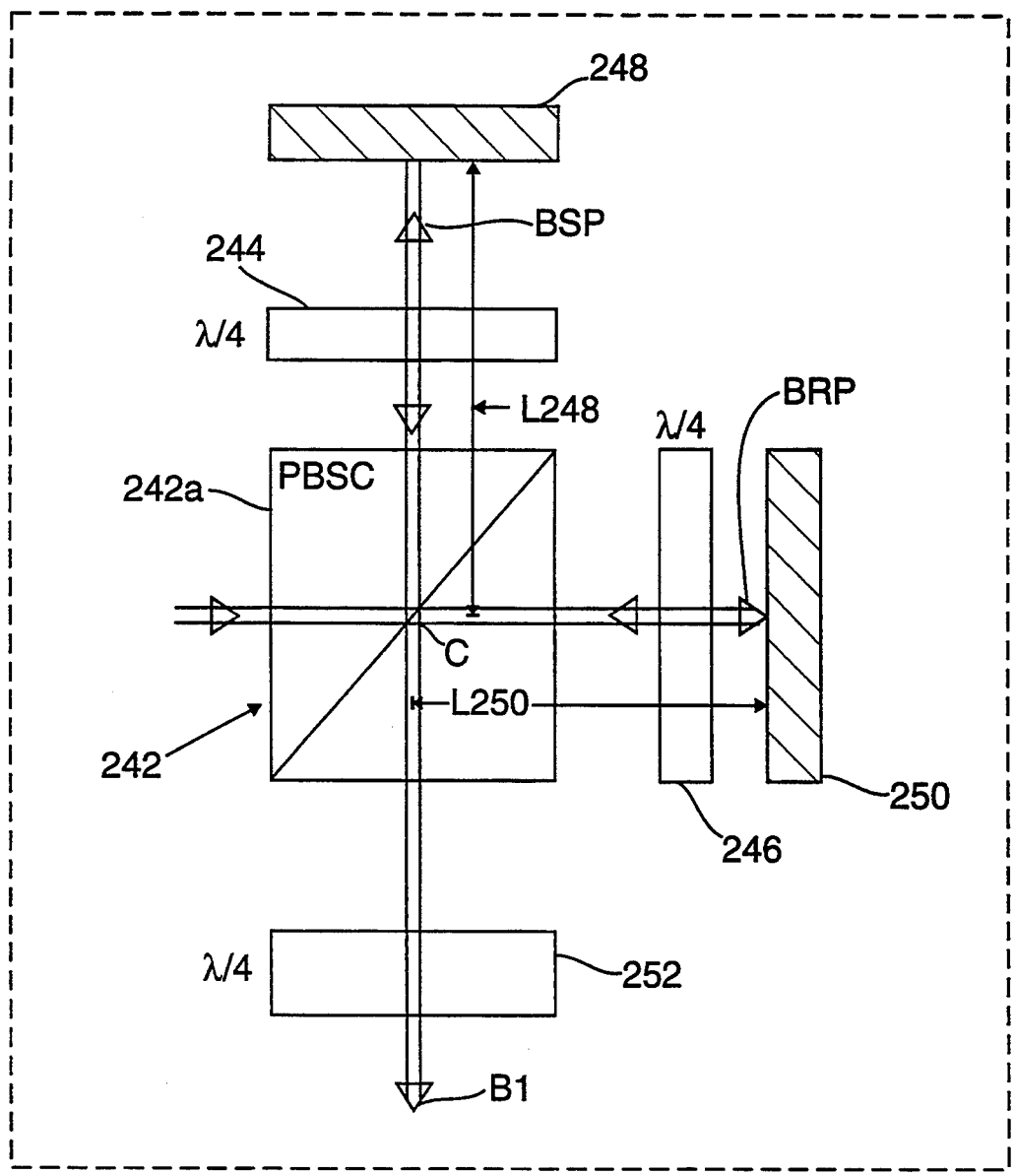
FIG. 12 is a schematic structural view of a polarizing frequency shifter of FIG. 11.

FIG. 11 is a block diagram of an apparatus of a third embodiment utilizing direct frequency modulation of a laser diode. FIG. 12 is a schematic structural view of a polarizing frequency shifter of FIG. 11 for use in conjunction with the third embodiment. The parts identical with those of FIGS. 1 and 2 will be designated by the same reference numerals but with an addition of 200. Furthermore, the description of identical parts will be omitted.

The apparatus shown in FIG. 11 is generally the same as the one of FIG. 1 with the following exceptions: piezo-transducer (PZT) 26, piezo controller 28, and feedback FS from electronic signal processing unit 34 to piezoelectric controller 28 are eliminated, while some new elements are introduced. The new elements are a current controller 227 and a triangular wave generator 229, and feedback FS1 from electronic signal processing unit 234 to current controller 227 (FIG. 11). Current controller 227 is connected to laser diode 222 and to triangular wave generator 229. In fact, current controller 227 is an element of apparatus of FIG. 1, as well, but it has not been shown.

A polarizing frequency shifter (PFS) 224 is the same as PFS 24 with the exception that PZT 26 is removed.

The apparatus of the third embodiment of FIGS. 11 and 12 operates similarly to that of the first embodiment with the exception that phase modulation of laser beam B which is supplied to PFS 224 is produced by direct frequency modulation of this beam in laser diode 222. In this case phase modulation in PFS 224 may be expressed by the following formula:

$$\phi(T) = \phi_0 + 2\pi f t$$

$$f = 4\beta \cdot (\Delta L/C) I_a f_o$$

$$\phi_o = 2\pi (\Delta L/C) \nu_o,$$

where $\phi_o$ is a statical phase shift, f is a PFS frequency, $\beta$ is a frequency-to-current conversion factor of laser diode 222, $\Delta L$ is an optical-path difference in PFS 224, $I_a$ is an amplitude of current modulation produced by triangular wave generator 229, $f_o$ is a frequency of the triangular wave, and $\nu_o$ is an optical frequency of laser diode 222.

As far as PFS 224 is concerned, it operates in the same manner as PFS 24, with the exception that both mirrors 248 and 250 are not subject to vibrations because the beam is modulated not by vibration of the mirrors but by directly changing the frequency of laser diode 222.

Thus, it has been shown that the invention provides methods and apparatus for non-invasive precision phase-sensitive measurement of blood glucose. These methods and apparatus do not involve the use of mechanically moving parts, result in low-noise measurements, operate in the frequency range beyond that of mechanical vibrations, are suitable for use at home or as a portable blood monitoring device, utilize processing electronics which allow glucose-level measurements through high-scattering tissue, and are not restricted for use with an eye but applicable to other blood-carrying body parts. Advantageously also, the device and methods use a single near infrared light source, e.g., a single laser diode. In addition, the device obtains a measurement from perfused blood-carrying tissue in effective real time, rather than from aqueous eye humor in which changes in the glucose concentration may lag behind the blood glucose concentration by two hours.

Although the apparatus and the method have been shown and described in the form of specific embodiments, these embodiments, their parts, materials, and configurations have been given only as examples, and many other modifications of apparatus and method possible. For example, cartridge 59 may be removable, stored separately, and inserted when necessary, rather than be incorporated into apparatus 20. An LED (light-emitting diode) operating in a near-infrared region of the spectrum with adequate collimating lenses may be used instead of a laser diode. Apparatus 20 also may be equipped with memory 115 of sufficient capacity for storing a log of the patient's measurements, e.g., date, time and values. It also may be equipped for storing information regarding medication dosages administered, e.g., units of insulin, using a suitable keypad or other data entry system. In the case that apparatus 20 is constructed for use as a hospital or clinic-based unit, it may contain more substantial computing functions such as calibration data for each patient it will service, maintain a log of each patient's measurements and also may include additional electronic circuitry for improving the accuracy of measurements. For example, a feedback signal may be sent to the laser source to stabilize amplitude and phase noise variation of the laser beam.

The present invention is particularly useful for monitoring blood constituents which undergo short term changes, such as glucose, in the presence of other optically active blood or tissue constituents (whether less dominant than, e.g., glucose), e.g., protein, which either do not change or change very slowly with time. In the case where the other optically active components do change somewhat with time, short term and long term averaging techniques may be used to control the effects of a change in the other optically active components. Similarly, the start-up calibration using two or more invasive glucose measurements could be infrequently used, e.g., once a year or when the patient's weight has changed significantly.

The invention also may be useful for identifying the concentration of an optically active substance that is added to blood and selectively bonds to a desired blood constituent. For example, substances such as optically active monoclonal antibodies that bind to specific antigenic determinants of a selected blood constituent or cell subpopulation may be used. This provides for indirectly measuring noninvasively blood components that are not significantly or sufficiently optically active for diagnostic and therapeutic purposes.

One skilled in the art will appreciate that the present invention can be practiced by other than the described embodiments, which are presented for purposes of illustration and not of limitation.

I claim:

1. An apparatus for non-invasive precision phase-sensitive measurement of blood glucose concentration comprising:

a source which produces an infrared laser beam;

a polarizing frequency shifter having an optical input receiving said laser beam, a piezoelectric transducer imparting phase modulation to said laser beam, and an optical output which produces a polarized-modulated infrared laser beam;

a piezoelectric controller operatively connected to said piezoelectric transducer to operate the piezoelectric transducer at a selected modulation frequency;

an optical transducer which has a glucose measuring head and an optical input receiving said polarized-modulated infrared laser beam from said output of said polarizing frequency shifter and an output providing a reference electric signal, said glucose measuring head having a space for receiving a blood sample and generating a probe electric signal corresponding polarized component of the polarized-modulated laser beam passing through the blood sample and a thickness measurement signal corresponding to a thickness of said blood sample; and an electronic signal processing unit which has an input which is electrically connected to said optical transducer for receiving said reference electric signal and inputs which are electrically connected to said glucose measuring head for receiving said probe electric signal and thickness measurement signal, said electronic signal processing unit having a feedback loop to said piezoelectric controller for controlling the piezoelectric transducer and means for measuring a glucose concentration of said blood sample based on said probe and reference electric signals.

2. The apparatus of claim 1 wherein said polarizing frequency shifter comprises:

a polarizing beam splitter cube having a center, a beam input side and a beam output side which is perpendicular to said input side;

a first quarter-wave plate which is located on a side of said polarizing beam splitter cube which is opposite to said beam input side;

a second quarter-wave plate located on a side of said polarizing beam splitter cube which is opposite to said beam output side;

a third quarter-wave plate located on said beam output side of said polarizing beam splitter cube;

a first mirror which is located on an outer side of said first quarter-wave plate and a second mirror which is located on an outer side of said second quarter-wave plate, wherein said piezoelectrical transducer is attached to one of the first and second mirrors;

wherein the beam splitter cube input side, first quarter wave plate and first mirror are on a first optical axis and the beam splitter cube output side, second quarter wave plate and second mirror are on a second optical axis and the difference between distances of said first and said second mirrors and said center of said polarizing beam splitter cube is smaller than a coherent length of said infrared laser beam.

3. The apparatus of claim 1 wherein said electronic signal processing unit comprises a phase-sensitive homodyne receiver which receives said reference electrical signal and said probe electrical signal, a microcontroller connected to said phase-sensitive homodyne receiver, and a memory connected to said microcontroller.

4. The apparatus of claim 3 further comprising:

an audio transmitter connected to said microcontroller;

an analog-to-digital converter connected to said microcontroller; and a display unit connected to said analog-to-digital converter.

5. The apparatus of claim 1 wherein the blood sample is a blood carrying body part and said glucose measuring head comprises:

a housing having said space for receiving said blood-carrying body part;

an optical measurement signal input located on one side of said space for receiving said probe optical signal; and a photoreceiver located on a side of said space opposite to said one side, the photoreceiver having an output signal that is said probe electrical signal.

6. The apparatus of claim 5 wherein the glucose measuring head further comprises:

fixation means for fixing said blood-carrying body part in position relative to said space; and compression means for compressing said blood-carrying body part.

7. The apparatus of claim 1 wherein said optical transducer further comprises an optical attenuator, a reference calibration cartridge with at least two cells containing glucose solutions of different concentrations, a reference polarizer, and a reference sensor, wherein said optical attenuator, reference calibration cartridge, reference polarizer and reference sensor are spatially arranged sequentially on a common optical axis aligned with said reference optical output side.

8. The apparatus of claim 1 wherein said optical transducer comprises:

a beam splitter cube having an optical input side for receiving said polarized-modulated infrared laser beam which is split into a reference optical signal and a probe optical signal, a reference optical output side, and a measurement optical output side; and a measurement sensor in the form of a balanced receiver which produces at its output said probe electrical signal, wherein the glucose measuring head is disposed between the measurement sensor and said measurement optical output side.

9. The apparatus of claim 8 wherein said balanced receiver is a photoreceiver.

10. The apparatus of claim 9 wherein said polarizing frequency shifter comprises:

a polarizing beam splitter cube having a center, a beam input side and a beam output side which is perpendicular to said input side;

a first quarter-wave plate which is located on a side of said polarizing beam splitter cube which is opposite to said beam input side;

a second quarter-wave plate located on a side of said polarizing beam splitter cube which is opposite to said beam output side;

a first mirror which is located on an outer side of said first quarter-wave plate and a second mirror which is located on an outer side of said second quarter-wave plate wherein said piezoelectric transducer is attached to one of the first and second mirrors;

wherein the beam Splitter cube input side, first quarter-wave plate and first mirror are on a first optical axis and the beam splitter cube output side, second quarter-wave plate and second mirror are on a second optical axis and the difference between distances of said first and said second mirrors and said center of said polarizing beam splitter cube is smaller than a coherent length of said infrared laser beam.

11. The apparatus of claim 10 wherein said photoreceiver comprises a photodetector having an electrical output and producing an output signal, a filter unit including a high pass and a low pass filter connected in parallel, where the filter unit is connected in series with the photodetector electrical output, and a division amplifier having an input receiving the filtered photodetector output signal, said photodetector output signal corresponding to said probe optical signal from said glucose measuring head, said division amplifier having an output.

12. The apparatus of claim 11 wherein said electronic signal processing unit comprises a phase-sensitive homodyne receiver which receives said reference electrical signal and said probe electrical signal, a microcontroller connected to said phase-sensitive homodyne receiver, and a memory connected to said microcontroller.

13. The apparatus of claim 12 wherein the blood sample is a blood carrying body part and said glucose measuring head comprises:

a housing having said space for receiving said blood-carrying body part;

an optical measurement signal input located on one side of said space for receiving said probe optical signal, said photoreceiver being located on a side of said space opposite to said one side;

fixation means for fixing said blood-carrying body part in position relative to said space; and compression means for compressing said blood-carrying body part.

14. The apparatus of claim 13 wherein said housing space further comprises a shape for receiving a finger.

15. The apparatus of claim 8 wherein said optical transducer further comprises an optical attenuator, a reference calibration cartridge with at least two cells containing glucose solutions of different concentrations, a reference polarizer, and a reference sensor, wherein said optical attenuator, reference calibration cartridge, reference polarizer and reference sensor are spatially arranged sequentially on a common optical axis aligned with said reference optical output side.

16. The apparatus of claim 8 wherein said measurement sensor comprises:

a beam splitter plate which receives said probe optical signal from said glucose measuring head and splits said probe optical signal into a first component and a second component;

a polarizer and first photodetector, said first component being passed to said first photodetector through said polarizer, said first photodetector having an output corresponding to the polarized component;

a second photodetector which receives said second component from said beam splitter plate having an output corresponding to a depolarized component of the probe optical signal passed through the blood sample;

a difference amplifier having a first input and a second input and an output, said first input of said difference amplifier being connected to said first photodetector output and said second input of said difference amplifier being connected to said second photodetector output;

a division amplifier having a first input, a second input, and an output; and a low-pass filter electrically connected between said second photodetector and said second input of said division amplifier, said output of said difference amplifier being connected to said first input of said division amplifier.

17. The apparatus of claim 8 wherein the blood sample is a blood-carrying body part and said glucose measuring head comprises:

a housing having said space for receiving said blood-carrying body part;

an optical measurement signal input located on one side of said space for receiving said probe optical signal, said balanced receiver being located on a side of said space opposite to said one side; and a sensor operatively connected to said housing for measuring said thickness of said blood-carrying body part for producing said thickness measurement signal.

18. The apparatus of claim 17 wherein said glucose measuring head further comprises:

fixation means for fixing said blood-carrying body part in position relative to said space; and compression means for compressing said blood-carrying body part.

19. The apparatus of claim 17 wherein said housing space further comprises a shape for receiving a finger.

20. The apparatus of claim 17 wherein said optical transducer further comprises a polarization preserving fiber optic link connecting said glucose measuring head optical measurement signal input to said measurement optical output side of said beam splitter cube.

21. The apparatus of claim 17, wherein said optical transducer further comprises a polarization preserving fiber optic link connecting said glucose measuring head optical measurement signal input to said measurement optical output side of said beam splitter cube, a head appliance which can be attached to the subject's head and wherein said glucose measuring head is made in the form of a resilient U-shape clip for inserting into said U-shaped clip an ear lobule of another ear of said subject, said U-shaped clip having a first leg and a second leg, said first leg supporting said polarization preserving fiber-optic link and said second leg supporting said balanced receiver and said thickness measurement sensor, so that during operation of said apparatus said phase-modulated infrared laser beam is transmitted to said balanced receiver through said ear lobule.

22. The apparatus of claim 17 wherein said balanced receiver is a photoreceiver.

23. The apparatus of claim 22 wherein said polarizing frequency shifter comprises:

a polarizing beam splitter cube having a center, a beam input side and a beam output side which is perpendicular to said input side;

a first quarter-wave plate which is located on a side of said polarizing beam splitter cube which is opposite to said beam input side;

a second quarter-wave plate located on a side of said polarizing beam splitter cube which is opposite to said beam output side;

a first mirror which is located on an outer side of said first quarter-wave plate and a second mirror which is located on an outer side of said second quarter-wave plate wherein said piezoelectric transducer is attached to one of the first and second mirrors;

wherein the beam splitter cube input side, first quarter-wave plate and first mirror are on a first optical axis and the beam splitter cube output side, second quarter-wave plate and second mirror are on a second optical axis and the difference between distances of said first and said second mirrors and said center of said polarizing beam splitter cube is smaller than a coherent length of said infrared laser beam.

24. The apparatus of claim 23 wherein said photoreceiver comprises a photodetector having an electrical output and producing an output signal, a filter unit including a high pass and a low pass filter connected in parallel, where the filter unit is connected in series with the photodetector electrical output, and a division amplifier having an input receiving the filtered photodetector output signal, said photodetector output signal corresponding to said probe optical signal from said glucose measuring head, said division amplifier having an output.

25. The apparatus of claim 17 wherein said electronic signal processing unit comprises a phase-sensitive homodyne receiver which receives said reference electrical signal and said probe electrical signal, a microcontroller connected to said phase-sensitive homodyne receiver, and a memory connected to said microcontroller.

26. The apparatus of claim 25 wherein said housing space further comprises a shape for receiving a finger.

27. The apparatus of claim 8 wherein said polarizing frequency shifter comprises:

a polarizing beam splitter cube having a center, a beam input side and a beam output side which is perpendicular to said input side;

a first quarter-wave plate which is located on a side of said polarizing beam splitter cube which is opposite to said beam input side;

a second quarter-wave plate located on a side of said polarizing beam splitter cube which is opposite to said beam output side;

a third quarter-wave plate located on said beam output side of said polarizing beam splitter cube;

a first mirror which is located on an outer side of said first quarter-wave plate and a second mirror which is located on an outer side of said second quarter-wave plate wherein said piezoelectric transducer is attached to one of the first and second mirrors;

wherein the beam splitter cube input side, first quarter wave plate and first mirror are on a first optical axis and the beam splitter cube output side, second quarter wave plate and second mirror are on a second optical axis and the difference between distances of said first and said second mirrors and said center of said polarizing beam splitter cube is smaller than a coherent length of said infrared laser beam.

28. The apparatus of claim 27 wherein said measurement sensor comprises:

a beam splitter plate which receives said probe optical signal from said glucose measuring head and splits said probe optical signal into a first component and a second component;

a polarizer and first photodetector, said first component being passed to said first photodetector through said polarizer, said first photodetector having an output corresponding to the polarized component;

a second photodetector which receives said second component from said beam splitter plate having an output corresponding to a depolarized component of the probe optical signal passed through the blood sample;

a difference amplifier having a first input and a second input and an output, said first input of said difference amplifier being connected to said first photodetector output and said second input of said difference amplifier being connected to said second photodetector output;

a division amplifier having a first input, a second input, and an output; and a low-pass filter electrically connected between said second photodetector and said second input of said division amplifier, said output of said difference amplifier being connected to said first input of said division amplifier.

29. The apparatus of claim 28 wherein said electronic signal processing unit comprises a phase-sensitive homodyne receiver which receives said reference electrical signal and said probe electrical signal, a microcontroller connected to said phase-sensitive homodyne receiver, and a memory connected to said microcontroller.

30. The apparatus of claim 29 further comprising: an audio transmitter connected to said microcontroller;

an analog-to-digital converter connected to said microcontroller; and a display unit connected to said analog-to-digital converter.

31. The apparatus of claim 30 wherein the blood sample is a blood-carrying body part and said glucose measuring head comprises:

a housing having said space for receiving said blood-carrying body part;

an optical measurement signal input located on one side of said space for receiving said probe optical signal, said balanced receiver being located on a side of said space opposite to said one side;

a sensor operatively connected to said housing for measuring said thickness of said blood-carrying body part for producing said thickness measurement signal;

fixation means for fixing said blood-carrying body part in position relative to said space; and compression means for compressing said blood-carrying body part.

32. The apparatus of claim 31 wherein said housing space further comprises a shape for receiving a finger.

33. The apparatus of claim 32 wherein said optical transducer further comprises a polarization preserving fiber optic link connecting said glucose measuring head optical measurement signal input to said measurement optical output of said beam splitter cube.

34. The apparatus of claim 31, wherein said optical transducer further comprises a polarization preserving fiber optic link connecting said glucose measuring head optical measurement signal input to said measurement optical output of said beam splitter cube, a head appliance which can be attached to the subject's head and supports a microphone connected to an audio transmitter and located near one ear of said subject when said head appliance is attached to the subject's head, and wherein said glucose measuring head is made in the form of a resilient U-shape clip for inserting into said U-shaped clip an ear lobule of another ear of said subject, said U-shaped clip having a first leg and a second leg, said first leg supporting said polarization preserving fiber-optic link and said second leg supporting said balanced receiver and said thickness measurement sensor, so that during operation of said apparatus said phase-modulated infrared laser beam is transmitted to said balanced receiver through said ear lobule.

35. A method for non-invasive precision phase-sensitive measurement of blood glucose concentration comprising:
producing an infrared laser beam;
passing said laser beam through a polarizing frequency shifter including a piezoelectric transducer, controlling the piezoelectric transducer to operate at a selected modulation frequency to impart phase modulation to said laser beam, thereby providing a polarized-modulated infrared laser beam;
separating the polarized-modulated infrared laser beam into a probe beam and a reference beam;
passing the probe beam through a blood sample, detecting the probe beam after passage through the blood sample, and generating a probe electric signal corresponding a the polarized component of the polarized-modulated laser beam passed through the blood sample;
detecting the reference beam and generating a reference electric signal corresponding to a polarized component of the reference beam;
determining a thickness of said blood sample and generating a thickness measurement signal corresponding to said thickness; and
processing said reference electric signal, said probe electric signal and thickness measurement signal and determining a glucose concentration in said blood sample based on said probe and reference electric signals, feeding back a signal for controlling the piezoelectric transducer modulation of the laser beam.

36. The method of claim 35 wherein separating said laser beam further comprises passing said laser beam into a beam splitter and splitting said laser beam into a reference beam and a probe beam, wherein detecting said probe beam further comprises passing said probe beam into a balanced receiver which produces at its output said probe electrical signal.

37. The method of claim 36 wherein passing said probe beam into said balanced receiver further comprises passing said probe beam into a photoreceiver.

38. The method of claim 36 wherein passing said laser beam through said polarizing frequency shifter further comprises:
splitting said laser into a first beam and a second beam by passing the laser beam into a polarizing beam splitter having a center;
passing the first beam through a first quarter-wave plate and reflecting the first beam off a first mirror back through the first quarter wave plate;
passing the second beam through a second quarter-wave plate and reflecting the second beam off a second mirror back through the second quarter wave plate;
attaching the piezoelectric transducer to one of the first and second mirrors to impart a phase modulation to one of the first and second beams respectively;
combining the reflected first and second beams on a common optical axis and passing the combined beams through a third quarter-wave plate; and
spacing and orienting the first and second mirrors so that the difference between distances of said first and said second mirrors and said center of said polarizing beam splitter is smaller than a coherent length of said infrared laser beam.

39. The method of claim 38 wherein detecting said probe beam further comprises passing said probe beam to a photodetector having an electrical output, low-pass and high-pass filtering said photodetector electrical output, and passing said filtered output to a division amplifier.

40. The method of claim 39 wherein processing said reference electrical signal and said probe electrical signal further comprises passing said reference electrical signal and said probe electrical signal into a phase-sensitive homodyne receiver, controlling said homodyne receiver to determine a phase shift, and determining from the determined phase shift the glucose concentration of the blood sample.

41. The method of claim 40 wherein the blood sample is a blood-carrying body part, the method further comprising:
providing a housing having a space for receiving said blood-carrying body part;
passing the probe beam through said space for intersecting said blood carrying body part; and
measuring said thickness of said blood-carrying body part for producing said thickness measurement signal.

42. The method of claim 40 further comprising fixing said blood-carrying body part in said space and compressing said blood-carrying body part for obtaining the glucose concentration measurement.

43. The method of claim 41 further comprising shaping said housing for receiving a finger.

44. The method of claim 36 further comprising calibrating the output signal using a reference calibration cartridge having at least two cells containing glucose solutions of different concentrations, by determining signal outputs of the balanced receiver for each of the two known concentrations, and adjusting a relation between the determined signal outputs to the known concentration to calibrate the glucose measurement.

45. The method of claim 35 wherein passing said laser beam through said polarizing frequency shifter further comprises:
splitting said laser beam into a first beam and a second beam by passing the laser beam into a polarizing beam splitter having a center;
passing the first beam through a first quarter-wave plate and reflecting the first beam off a first mirror back through the first quarter wave plate;
passing the second beam through a second quarter-wave plate and reflecting the second beam off a second mirror back through the second quarter wave plate;

attaching the piezoelectric transducer to one of the first and second mirrors to impart a phase modulation to one of the first and second beams respectively;

combining the reflected first and second beams on a common optical axis and passing the combined beams through a third quarter-wave plate; and spacing and orienting the first and second mirrors so that the difference between distances of said first and said second mirrors and said center of said polarizing beam splitter is smaller than a coherent length of said infrared laser beam.

46. The method of claim 45 wherein detecting the probe beam after passage through the blood sample comprises:

splitting said probe beam into a first optical component and a second optical component;

passing said first optical component through a polarizer to a first photodetector, said first photodetector having an output corresponding to a polarized component of the probe beam;

passing said second optical component to said second photodetector having an output corresponding to a depolarized component of the probe beam; and low-pass filtering the output of the second photodetector and differentially amplifying the output of the first photodetector and the low-pass filtered output of the second photodetector.

47. The method of claim 46 wherein processing said reference electrical signal and said probe electrical signal further comprises passing said reference electrical signal and said probe electrical signal into a phase-sensitive homodyne receiver, and controlling said homodyne receiver to determine a phase shift and determining from the determined phase shift the glucose concentration of the blood sample.

48. The method of claim 47 wherein the blood sample is a blood-carrying body part, the method further comprising:

providing a housing having a space for receiving said blood-carrying body part;

passing the probe beam through said space for intersecting said blood carrying body part; and measuring said thickness of said blood-carrying body part for producing said thickness measurement signal.

49. The method of claim 48 further comprising fixing said blood-carrying body part in said space and compressing said blood-carrying body part for obtaining the glucose concentration.

50. The method of claim 48 further comprising shaping said housing space for receiving a finger.

51. The method of claim 50 further comprising coupling said probe beam to said housing by using a polarization preserving fiber optic link.

52. The method of claim 48 further comprising coupling said probe beam to said housing by using a polarization preserving fiber optic link, attaching said housing to a head appliance which can be attached to the subject's head and configuring the housing shape in the form of a resilient U-shape clip for inserting into said U-shaped clip an ear lobule of said subject and supporting said polarization preserving fiber-optic link on said U-shaped clip.

53. The method of claim 35 wherein passing said laser beam through said polarizing frequency shifter further comprises:

splitting said laser beam into a first beam and a second beam by passing the laser beam into a polarizing beam splitter having a center;

passing the first beam through a first quarter-wave plate and reflecting the first beam off a first mirror back through the first quarter wave plate;

passing the second beam through a second quarter-wave plate and reflecting the second beam off a second mirror back through the second quarter wave plate;

attaching the piezoelectric transducer to one of the first and second mirrors to impart a phase modulation to one of the first and second beams respectively;

combining the reflected first and second beams on a common optical axis and passing the combined beams through a third quarter-wave plate; and spacing and orienting the first and second mirrors so that the difference between distances of said first and said second mirrors and said center of said polarizing beam splitter is smaller than a coherent length of said infrared laser beam.

54. The method of claim 35 wherein detecting the probe beam after passage through the blood sample comprises:

splitting said probe beam into a first optical component and a second optical component;

passing said first optical component through a polarizer to a first photodetector, said first photodetector having an output corresponding to a polarized component of the probe beam;

passing said second optical component to a second photodetector having an output corresponding to a depolarized component of the probe beam; and low-pass filtering the output of the second photodetector and differentially amplifying the output of the first photodetector and the low-pass filtered output of the second photodetector.

55. The method of claim 35 wherein processing said reference electrical signal and said probe electrical signal further comprises passing said reference electrical signal and said probe electrical signal into a phase-sensitive homodyne receiver, and controlling said homodyne receiver to determine a phase shift and determining from the determined phase shift the glucose concentration of the blood sample.

56. The method of claim 36 wherein the blood sample is a blood-carrying body part, the method further comprising:

providing a housing having a space for receiving said blood-carrying body part;

passing the probe beam through said space for intersecting said blood carrying body part; and measuring a thickness of said blood-carrying body part for producing said thickness measurement signal.

57. The method of claim 56 further comprising fixing said blood-carrying body part in said space and compressing said blood-carrying body part for obtaining the glucose concentration.

58. The method of claim 56 further comprising shaping said housing space for receiving a finger.

59. The method of claim 56 further comprising coupling said probe beam to said housing by using a polarization preserving fiber optic link.

60. The method of claim 56 further comprising coupling said probe beam to said housing by using a polarization preserving fiber optic link, attaching said housing to a head appliance which can be attached to the subject's head and configuring the housing shape in the form of a resilient U-shape clip for inserting into said U-shaped clip an ear lobule of said subject and supporting said polarization preserving fiber-optic link on said U-shaped clip.

61. The method of claim 56 wherein passing said probe beam into said balanced receiver further comprises passing said probe beam into a photoreceiver.

62. The method of claim 59 wherein passing said laser beam through said polarizing frequency shifter further comprises:
   splitting said laser into a first beam and a second beam by passing the laser beam into a polarizing beam splitter having a center;
   passing the first beam through a first quarter-wave plate and reflecting the first beam off a first mirror back through the first quarter wave plate;
   passing the second beam through a second quarter-wave plate and reflecting the second beam off a second mirror back through the second quarter wave plate;
   attaching the piezoelectric transducer to one of the first and second mirrors to impart a phase modulation to one of the first and second beams respectively;
   combining the reflected first and second beams on a common optical axis and passing the combined beams through a third quarter-wave plate; and
   spacing and orienting the first and second mirrors so that the difference between distances of said first and said second mirrors and said center of said polarizing beam splitter is smaller than a coherent length of said infrared laser beam.

63. The method of claim 62 wherein detecting said probe beam further comprises passing said probe beam to a photodetector having an electrical output, low-pass and high-pass filtering said photodetector electrical output, and passing said filtered output to a division amplifier.

64. The method of claim 56 wherein processing said reference electrical signal and said probe electrical signal further comprises passing said reference electrical signal and said probe electrical signal into a phase-sensitive homodyne receiver, controlling said homodyne receiver to determine a phase shift, and determining from the determined phase shift the glucose concentration of the blood sample.

65. The method of claim 35 wherein the blood sample is a blood-carrying body part, the method further comprising:
   providing a housing having a space for receiving said blood-carrying body part;
   passing the probe beam through said space for intersecting said blood carrying body part; and
   measuring said thickness of said blood-carrying body part for producing said thickness measurement signal.

66. The method of claim 65 further comprising fixing said blood-carrying body part in said space and compressing said blood-carrying body part for obtaining the glucose concentration.

67. The method of claim 65 further comprising shaping said housing for receiving a finger.

68. The method of claim 35 further comprising calibrating the output signal using a reference calibration cartridge having at least two cells containing glucose solutions of different concentrations, by determining the signal outputs for each of the two known concentrations, and adjusting a relation between the determined signal outputs to the known concentrations to calibrate the glucose measurement.

* * * * *